(12) United States Patent
Okano et al.

(10) Patent No.: US 6,733,648 B2
(45) Date of Patent: May 11, 2004

(54) ELECTROPHORESIS CHIP

(75) Inventors: Kazunori Okano, Shiki (JP); Kenji Yasuda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 137 days.

(21) Appl. No.: 10/084,505

(22) Filed: Feb. 28, 2002

(65) Prior Publication Data

US 2003/0111348 A1 Jun. 19, 2003

(30) Foreign Application Priority Data

Dec. 18, 2001 (JP) ........................................ 2001-385018

(51) Int. Cl.$^7$ ............................................ G01N 27/453
(52) U.S. Cl. ........................ 204/606; 204/616; 204/620
(58) Field of Search ................................ 204/600, 606, 204/615, 616, 619, 620, 450, 456, 465, 466, 470

(56) References Cited

U.S. PATENT DOCUMENTS

| | | | | |
|---|---|---|---|---|
| 4,443,319 A | * | 4/1984 | Chait et al. | 204/616 |
| 4,666,581 A | * | 5/1987 | Itoh et al. | 204/616 |
| 5,904,824 A | * | 5/1999 | Oh | 204/601 |

FOREIGN PATENT DOCUMENTS

| | | | |
|---|---|---|---|
| JP | 06-169756 | * | 6/1994 |
| JP | 2000-46797 | * | 2/2000 |
| JP | 2000-214132 | * | 8/2000 |
| JP | 2001-157855 | * | 6/2001 |
| JP | 2001-514746 | * | 9/2001 |
| JP | 2002-5887 | * | 1/2002 |
| JP | 2002-18278 | * | 1/2002 |
| WO | WO 98/39645 | | 3/1998 |
| WO | WO 01/54810 | * | 8/2001 |

OTHER PUBLICATIONS

Patent Abstract of Japan for 2002-145916, May 2002.*
Xiaohua Huang, Mark A. Quesada and Richard A. Mathies, "Capillary Array Electrophoresis Using Laser–Excited Confocal Fluorescence Detection", Anal. Chem. 1992,.64, pp. 967–972.
D. Jed Harrison, Andreas Manz, Zhonghui Fan, Hans Ludi and H, Michael Widmer, "Capillary Electrophoresis and Sample Injection Systems Integrated on a Planar Glass Chip", Analytical Chemistry, 1992, 64, 1992 American Chemical Society, pp. 1926–1932.
Adam T. Woolley and Richard A. Mathies, "Ultra–High––Speed DNA Sequencing Using Capillary Electrophoresis Chips", Analytical Chemistry, vol. 67, No. 20, Oct. 15, 1995, pp. 3676–3680.
Office Action dated Aug. 5, 2003, from the Japanese Patent Office issued in corresponding Japanese patent application (untranslated).

* cited by examiner

*Primary Examiner*—Kaj K. Olsen
(74) *Attorney, Agent, or Firm*—Reed Smith LLP; Stanley P. Fisher, Esq.; Juan Carlos A. Marquez, Esq.

(57) ABSTRACT

An electrophoresis chip is provided, which facilitates injection of a very small quantity of samples. A hydrophobic region 62, a thin and long hydrophilic region, electrodes 67a and 67b are formed on a surface of a substrate 61. The hydrophilic region, and the electrodes are surrounded with the hydrophobic region 62. A gel 64 is formed in the hydrophilic region by dropping and superposing gel precursor solution. A slit 65 for sample addition is provided in the midway of the gel. A droplet 72 of sample solution is adhered to a tip of a needle 71 and, when the droplet is passed through the slit 65 in contact with the hydrophobic region 62, the droplet of the needle connects the gel 64 in such a way as to bury the slit 65 of the gel 64. Then, electrophoresis is carried out by applying electric fields to the electrodes 67a and 67b.

11 Claims, 16 Drawing Sheets

ELECTROPHORESIS CHIP

BACKGROUND OF THE INVENTION

1. Field of the Invention

The present invention relates to an apparatus for separating and analyzing a biological sample. More particularly, the invention relates to an electrophoresis chip suitably used for separation and analysis of a DNA fragment originated from a genome, polynucleotide fragment originated from RNA, protein, peptide, and the like, and to an electrophoresis apparatus.

2. Description of the Related Art

For analysis and division of a biological material, a separation technology using electrophoresis has been used most widely. For example, in a field of DNA analysis, DNA sequencing has frequently been carried out by using polyacrylamide gel electrophoresis. All genomic sequences of microbes such as *Escherichia coli* or yeast already have been unraveled. In the case of multicellular organisms, all genomes of *Caenorhabditis elegance* and *Drosophila melanogaster* have nearly been unraveled. Analysis of all human genomes will be completed in early 2000s. For an electrophoresis medium of electrophoresis having such high resolution, other than polyacrylamide gel, or high polymer consisting of derivatives of methyl cellulose or acrylamide polymer can be used.

In electrophoresis, generally, polymer is used as an electrophoresis medium, often by being filled a capillary made of silica-base material or plastic (Anal. Chem. (1992) 64,967–972). For DNA sample preparation and PCR product checking, an electrophoresis apparatus using agarose gel as an electrophoresis medium has frequently been used. Recently, a technology has been developed for forming a capillary structure by using glass or plastic for substrate, forming a very small groove in this substrate, and adhering another substrate as a surface cover to the substrate, and an electrophoresis chip using this technology has reached a stage of being put to practical use (Anal. Chem, (1992) 64,1926–1932, Anal. Chem. (1995) 67,3676–3680). In all of those methods, a structure is employed, in which an electrophoresis medium is formed in a plotted region substantially having a capillary form that is formed inside a capillary or a substrate (glass).

SUMMARY OF THE INVENTION

Conventionally, in electrophoresis for performing electrophoretic separation of a DNA fragment by high resolution as in the case of base sequence determination, an electrophoresis medium has formed in an area plotted in a groove form in the capillary or the substrate (glass). Generally, it is because when a gel is formed, a method of pouring gel precursor or polymer into a mold of a capillary or the like is an easy preparation method. In the conventional gel preparation method, a gel precursor or polymer must be poured for each capillary having an inner diameter of about 50 $\mu$m, and generally the following processes are necessary: (1) pouring of a gel precursor or polymer by connecting a pump to each capillary, and (2) disconnecting of a joined portion between the pump and the capillary through a valve. Particularly, there remains a problem in filling of a self-organization gel such as agarose. That is, since agarose has a property of being dissolved at a high temperature of 70 to 90° C., and gelled at a low temperature of 40 to 60° C., a problem of the agarose being formed into a gel in the pump occurs, and its processing is difficult. Also in the case of the polyacrylamide gel, since gelling occurs in the pump, there is a problem that maintaining a gel precursor flow passage including the pump, the valve and the like becomes extremely difficult. Consequently, the polyacrylamide gel has not been put to practical use yet. As another problem, there has been a serious one caused by inevitable presence of a pipe wall, while a gel shape can be easily reproduced according to accuracy of an inner diameter of the capillary as the mold. Specifically, since a sectional area is narrow when the gel precursor is gelled, and a surface area of a wall surface is wide with respect to a gel volume, gel shrinkage occurs following gelling to cause application of hysteresis. Thus, depending on an electrophoretic state, problems including a reduction in separation and, as a worst case, cutting-off of the gel have occurred.

In the case of the capillary system, although a sample capacity used for real electrophoretic separation is in a range of several tens to several hundreds of nL (nano-liter), because a technology of pouring a sample into the capillary is still poor, a sample capacity of several tens $\mu$L (microliter) is necessary at present. In other words, samples of several tens to several hundreds times as large as a sample capacity necessary for electrophoresis are now wasted. Thus establishment of a technology of handling a very small quantity of samples is an important technical task.

On the other hand, in the case of conventional agarose electrophoresis of a horizontal flat plate type, a gel may only be formed by pouring dissolved agarose into a mold having an open structure on an upper surface. Accordingly, gel preparation is easy. In the conventional agarose electrophoresis, gel is used by being dipped in buffer solution for electrophoresis. Since at least an upper surface of the gel is not in contact with a solid interface such as glass or plastic, an effect of the interface can be reduced. For sample injection, a method of adding a sample of increased specific gravity to a position having a concave surface formed during gel preparation is employed. Normally, a sample of several $\mu$L is used.

In the conventional agarose electrophoresis, a sample volume is in order of micro-liter, which is not in line with a tendency of technology that intends to perform analysis with high sensitivity by using a very small quantity of samples in the future. Actually, electrophoresis having separation performance similar to that of the agarose electrophoresis and using electrophoresis chips considered to be capable of being supplied in great quantity at low costs may become a mainstream. However, as in the case of the capillary system, a method of filling a groove (capillary) formed in a substrate with an electrophoresis medium (gel) and a technology for pouring a very small quantity of samples into the electrophoresis medium have not been established yet. Sample injection thus has taken a lot of effort, and there has been a problem of inevitably supplying a great quantity of samples more than necessary.

Objects of the present invention are to provide an electrophoresis chip capable of easily performing injection of a very small quantity of samples, an electrophoresis apparatus using the same, and a method of manufacturing the electrophoresis chip.

According to the invention, an electrophoresis chip is provided, which is constructed in a manner that a thin and long hydrophilic region, and a hydrophobic region are formed on a surface of an electrical insulating substrate, the hydrophobic region surrounding the hydrophilic region, a gel (electrophoresis medium) is formed in the hydrophilic region, and thus a shape of the gel can be formed with good reproducibility. As it is hydrophilic, gel precursor solution is adhered only to the hydrophilic region on the surface of the substrate. In the hydrophobic region, as it is repelled, the gel precursor solution can be easily removed. A quantity of the gel precursor solution left in the hydrophilic region is decided by hydrophobicity of the hydrophobic region, hydrophilicity of the hydrophilic region, and hydrophilicity of the gel precursor solution on the surface of the substrate. Thus, a fixed quantity of electrophoresis gel (electrophoresis medium) is formed in the hydrophilic region.

The produced electrophoresis chip can be used in a submarine form as in the case of agarose electrophoresis. The electrophoresis chip is placed in a humidifying box, and electrophoresis can be carried out in a manner that one surface of the gel is in contact with air or inert gas. Thus, compared with the conventional method of using a capillary, it is possible to suppress a reduction in resolution, which affects presence of a charged interface such as an electroosmotic flow.

A problem of injecting a very small quantity of sample solution can be solved by contriving pattern shapes of the hydrophobic region and the hydrophilic region formed on the surface of the substrate. The hydrophobic region and the hydrophilic region are provided on the surface of the substrate, the hydrophilic region with a thin and long shape being divided in a longitudinal direction. That is, first and second hydrophilic regions, which are thin and long in the longitudinal direction, are formed, and one tail end of the first hydrophilic regions is placed adjacently to that of the second hydrophilic region with a gap. The hydrophobic region is formed to surround the first and second hydrophilic regions. Gels (electrophoresis media) are formed in the first and second hydrophilic regions to construct first and second electrophoresis lanes.

Sample solution containing a sample is supplied to a region of the gap, a solution lane is formed by the sample solution between the gels (electrophoresis media) of the first and second hydrophilic regions, and thus the first and second electrophoresis lanes are connected with each other. The supplying of the sample solution to the region of the gap can be carried out by directly dropping the solution to a gap portion with a micro-dispenser. In another method of supplying sample solution, a thin pin (needle) hydrophilic only in a small part of its tip, and hydrophobic in other parts is dipped in the sample solution, lifted to form a droplet in the tip of the pin, and this droplet is brought into contact with the hydrophobic region on the substrate. Then, the droplet is held in a gap between the pin and the hydrophobic region formed on the substrate. By moving the pin, the droplet can be moved in an arbitrary direction. When the pin is passed through the gap portion provided in the gel (electrophoresis medium), the droplet is moved to the gels (electrophoresis media) of the first and second hydrophilic regions, the droplet is substantially held in the gap portion, and thus the supplying of the sample solution is completed.

Immediately after the formation of the solution lane by the droplet, electrophoresis can be carried out. By increasing/reducing a size of the gap, i.e., a width of the gap (widths of the first and second hydrophilic regions) and a length of a gap (gap length), and by holding the sample solution in the form of the droplet in the tip of the pin to supply the droplet to the gap, a sample of sub 1L can be injected.

Another electrophoresis chip of the invention is constructed in a manner that a plurality of thin and long hydrophilic regions are formed at predetermined intervals on surfaces of two electrical insulating substrates, and a hydrophobic region is formed on a surface other than the plurality of hydrophilic regions. The two substrates are fixed in parallel with a gap of several tens of $\mu$m to about 1 mm so as to place the hydrophilic regions oppositely to each other. Then, gel precursor solution may be poured into the gap to form a gel (electrophoresis medium) between the opposing hydrophilic regions of the two substrates. In this case, an effect of an interface is increased, but drying and shrinkage of the gel (electrophoresis medium) during electrophoresis can be effectively prevented.

In the foregoing, the hydrophobic region and the hydrophilic region were formed on the electrical insulating substrate. However, by reforming the surface of the electrical insulating hydrophobic substrate, it is possible to form a hydrophilic region of a desired shape on the hydrophobic substrate. Conversely, by reforming the surface of the electrical insulating hydrophilic substrate, it is possible to form a hydrophobic region so as to leave a hydrophilic region of a desired shape.

Embodiments of the invention are summarized as follows. An electrophoresis chip is provided, which includes an electrical insulating substrate and a electrophoresis medium formed to be linear on a surface of the substrate. In this case, a region adjacent to the electrophoresis medium on the surface of the substrate is hydrophobic.

(2) An electrophoresis chip is provided, which includes: an electrical insulating substrate having a linear hydrophilic region and a hydrophobic region adjacent to the hydrophilic region on a surface of the substrate; an electrophoresis medium formed on the hydrophilic region of the substrate by providing a gap of a predetermined length in one place in a longitudinal direction; and a pair of electrodes connected to both ends of the electrophoresis medium in the longitudinal direction.

(3) In the electrophoresis chip of (1) or (2), the substrate is glass.

(4) In the electrophoresis chip of (1) or (2), the electrophoresis medium is a gel.

(5) In the electrophoresis chip of (2), a sample is held in the gap.

(6) In the electrophoresis chip of (2), the gap is provided in a position close to one end from a center of the electrophoresis medium in the longitudinal direction.

(7) In the electrophoresis chip of (6), a length of a longer element medium of two element media of the electrophoresis medium divided into two parts is set in a range of 10 mm to 100 mm.

In the electrophoresis chip of the invention, to perform real electrophoresis separation, a necessary length of the electrophoresis medium is 10 mm at a minimum. In this case, it is possible to detect a difference between base lengths, one being twice as long as the other. In addition, to perform separation with accuracy of 10% of a length of a DNA, a length of 100 mm is enough.

(8) In the electrophoresis chip of (1) or (2), a width of the electrophoresis medium is set in a range of 0.1 mm to 5 mm.

To form a gel to be linear by a method of the invention, a width of 0.1 mm or more, preferably 0.2 mm or more, is necessary. If a width of an electrophoresis medium exceeds 5 mm, there is not much difference from a case where a planar gel is formed, losing an advantage of the method of the invention.

(9) In the electrophoresis chip of (1), a length of the gap in the longitudinal direction is set in a range of 0.2 mm to 1 mm.

To form a gap, a ratio between a width of the gel and the length of the gap is important. With a minimum width of 0.1 mm of the gel, a gap may be set in a range of about 0.1 mm to 0.2 mm. However, as the width is larger, an upper limit of the gap length becomes about 1 mm. If the gap length exceeds 1 mm, it is difficult to hold aqueous solution.

(10) An electrophoresis chip is provided, which includes an electrical insulating substrate having a plurality of linear hydrophilic regions formed almost in parallel on a surface and a hydrophobic region adjacent to the hydrophilic regions; a plurality of electrophoresis media, each formed on one of the plurality of hydrophilic regions of the substrate by providing a gap of a predetermined length in one place in a longitudinal direction; and a pair of electrodes, one being connected to one ends of the plurality of electrophoresis media and the other being connected to the other ends thereof.

(11) An electrophoresis chip is provided, which includes: an electrical insulating substrate having a plurality of linear hydrophilic regions formed almost in parallel on a surface of the substrate and a hydrophobic region adjacent to the hydrophilic regions; a plurality of electrophoresis media, each formed on one of the hydrophilic regions of the substrate by providing a gap of a predetermined length in one place in a longitudinal direction; and plural pairs of electrodes individually connected to both ends of the plurality of electrophoresis media.

(12) An electrophoresis chip is provided, which includes: an electrical insulating substrate having a thin and long hydrophilic region formed on a surface of the substrate and a hydrophobic region formed surrounding the hydrophilic region; and an electrophoresis medium formed on the hydrophilic region of the substrate by providing a gap of a predetermined length in one place in a longitudinal direction. In this case, an electrophoresis lane is formed by the electrophoresis medium and sample solution supplied to the gap.

DESCRIPTION OF THE PREFERRED EMBODIMENTS

Next, description will be made of the preferred embodiments of the present invention with reference to the accompanying drawings.

[First Embodiment]

Figure 1A:
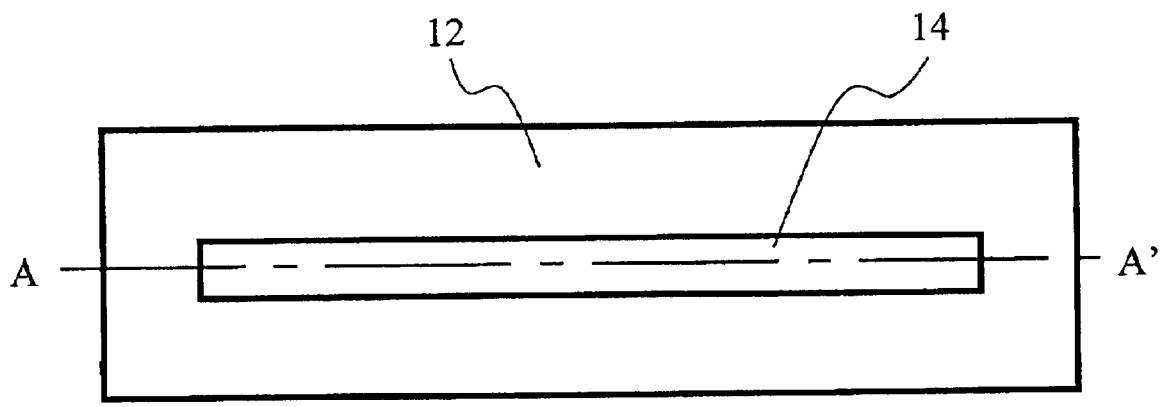
FIGS. 1A and 1B are views, each thereof showing a constitutional example of an electrophoresis chip according to the present invention.
Figure 1B:
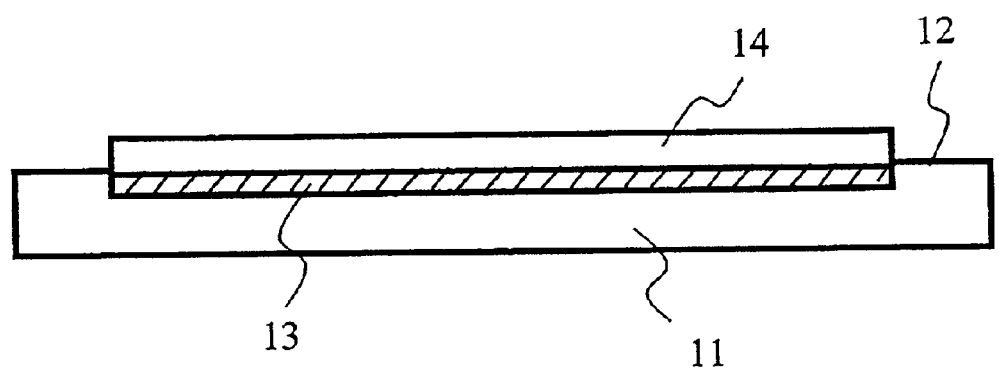
Figure 2A:
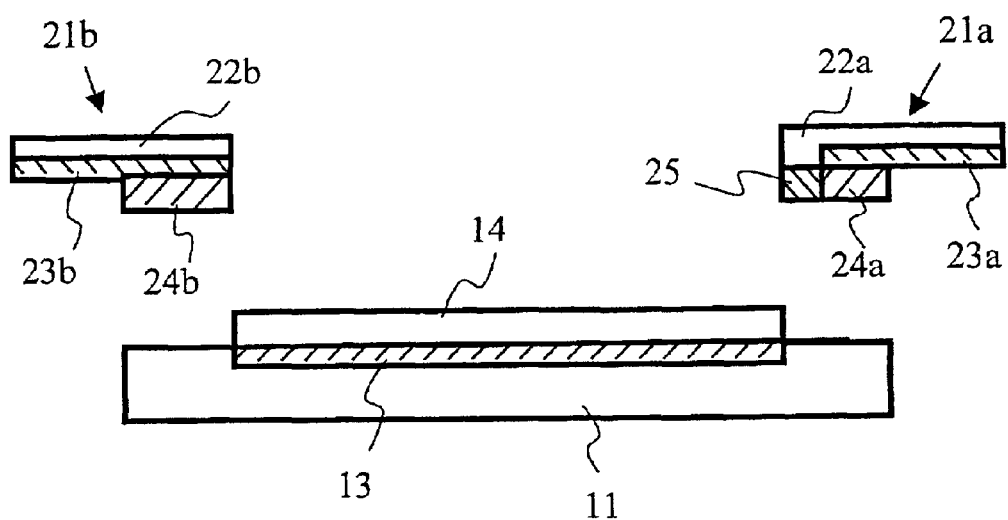
FIGS. 2A and 2B are explanatory views, each thereof showing a method of fixing electrodes to the electrophoresis chip.
Figure 2B:
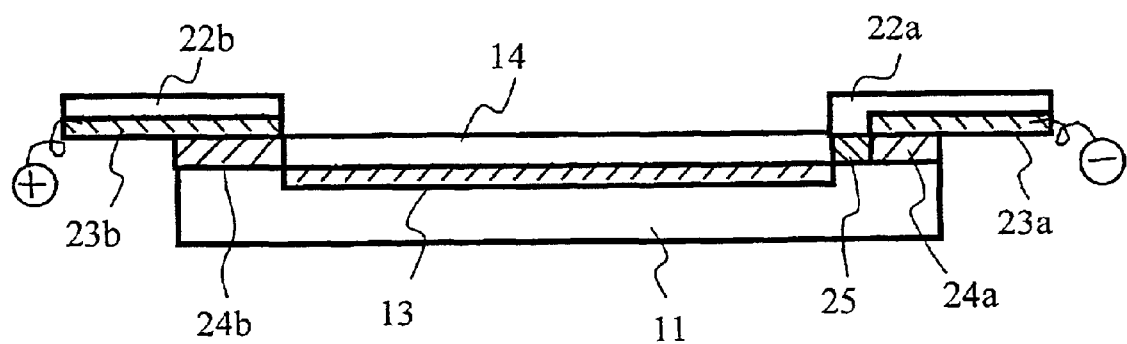

FIGS. 1A and 1B, and FIGS. 2A and 2B are explanatory views, each thereof showing a constitutional example of an electrophoresis chip of the invention. FIGS. 1A and 1B show electrophoresis chips before electrodes are fixed: FIG. 1A being a plan view; and FIG. 1B being a sectional view taken along a line A–A' in FIG. 1A. FIGS. 2A and 2B show a method of fixing the electrodes to the electrophoresis chips.

As shown in FIGS. 1A and 1B, the electrophoresis chip of the embodiment is constructed in such a manner that a hydrophobic region 12 and a hydrophilic region 13 are formed on a surface of a substrate 11, and an electrophoresis gel (electrophoresis lane) 14 is formed on the hydrophilic region 13. The hydrophilic region 13 is formed in a thin and long linear shape surrounded with the hydrophobic region 12. The hydrophilic region 13 has a width of 2 mm and a length of 8 cm. For easy formation, a width of the hydrophilic region 13 is in a range of 0.1 mm to 5 mm, and a length is in a range of 5 mm to 10 cm. However, a long electrophoresis lane of 30 cm can be formed. Generally, an electrophoresis length of 5 cm is enough for measuring DNAs with accuracy with which the DNAs having lengths different by 5% can be separated from each other. In the case of DNA sequencing, at least 700 bases must be separated with accuracy of one base, for which an electrophoresis length of about 30 cm is necessary. However, as a long time is required for electrophoresis, such a length is not proper in the electrophoresis chip using a preparation method of the invention because of a gel drying problem. This electrophoresis chip is suitably used for easily measuring a length of a DNA fragment as in the case of the agarose electrophoresis for measuring a length of a DNA fragment with an electrophoresis length set equal to/lower than 10 cm.

Many methods are available for forming the hydrophilic region 13 and the hydrophobic region 12. In the described case, a method was employed, in which the surface of the substrate 11 was first made fully hydrophobic by using Teflon base ink and, for the hydrophilic region 13, polymer was coated on a portion for forming a hydrophilic region, and then this portion was irradiated with UV to be made hydrophilic. A width of the hydrophilic region 13 was set to 2 mm. For forming the electrophoresis gel 14, dissolved agarose powder was added to 20 mM tris acetic acid buffer solution pH 8.0 (hereinafter, 0.5×TAE buffer solution) containing EDTA of 0.5 mM so as to set 0.8% (weight/volume), and one dissolved by heating at 90° C. was coated on the hydrophilic region 13 on the surface of the substrate 11. After excessive agarose solution was removed, the substrate was left at a room temperature, and then an agarose gel was formed on the hydrophilic region 13 in 2 to 5 min.

Here, the agarose gel was used for the electrophoresis medium. However, a similar electrophoresis chip can be produced by using a polyacrylamide gel. As an example, gel precursor solution containing 0.05 ml of 10% ammonium persulfate, and 4 micro-liter of TEMED as polymerization initiators in 10 ml of acrylamide monomer (T=7%, and C=5%) is dropped to the hydrophilic region. Then, the precursor solution is adhered to the hydrophilic region. Then, the substrate is immediately placed in a moist box filled with nitrogen gas, and polymerized for 30 min. Then, a polyacrylamide gel is formed on the hydrophilic region of the substrate.

Subsequently, electrodes are fixed for performing electrophoresis. Here, electrodes having removable structures are described. FIG. 2A is a view showing a state of the electrophoresis chip before the electrodes are fixed; FIG. 2B is a view showing a state of the electrophoresis chip after the electrodes are fixed. The electrodes 21a and 21b were provided in a manner that chrome was deposited on surfaces of electrode holding devices 22a and 22b made of glass or a silicon substrate, and the like, and then platinum deposition films 23a and 23b were formed by 30 nm or more in thickness. Note that if the platinum deposition films 23a and 23b are thin, electrode deterioration may occur during electrophoresis. Alternatively, the electrodes 21a and 21b may be formed by adhering a platinum plate or line onto the electrode holding devices 22a and 22b. Sponges 24a and 24b soaked with electrode solution are attached to part of the platinum deposition films 23a and 23b. For the electrode solution, general buffer solution for electrophoresis can be used. That is, 0.5 to 1×TE buffer solution can be used in the case of the agarose gel; and 0.5 to 1×TBE buffer solution in the case of the acrylamide gel. A sample is held at an end of one electrode 21a. In the example shown, a gel fragment 25 having a sample contained beforehand in the agarose gel is disposed in a bottom surface of the electrode 21a in contact with the sponge 24a soaked with the electrode solution.

For fixing the electrodes 21a and 21b to the electrophoresis chip, as shown in FIG. 2B, the electrode 21a is fixed on the substrate 11 so as to bring the gel fragment 25 containing the sample into contact with an end of the electrophoresis gel 14, and the electrode 21b is fixed on the substrate 11 so as to bring the sponge 24b soaked with the electrode solution into contact with the other end of the electrophoresis gel 14. In this case, the electrode 21a of the side having the gel fragment 25 containing the sample is structured to prevent the platinum deposition film 23a from being brought into direct contact with the electrophoresis gel 14. Thus, by fixing the electrodes 21a and 21b to the electrophoresis chip, and by applying voltages with the electrode 21a close to the sample set as a negative electrode and the electrode 21b away from the sample set as a positive electrode, the sample held by the gel fragment 25 is moved to the electrophoresis gel 14 as an electrophoresis medium, and separated by its physical properties.

[Second Embodiment]

Figure 3A:
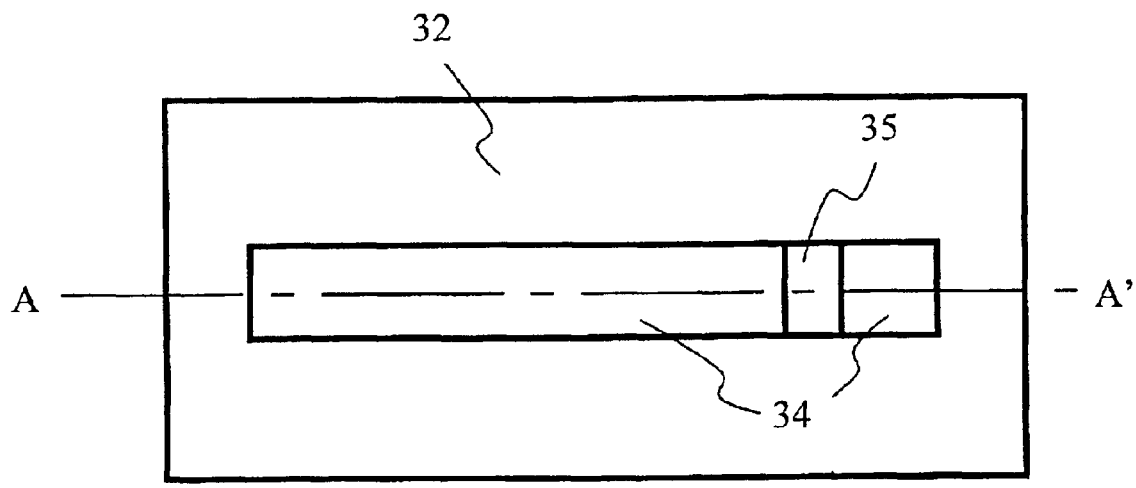
FIGS. 3A and 3B are explanatory views, each thereof showing another constitutional example of an electrophoresis chip according to the invention.
Figure 3B:
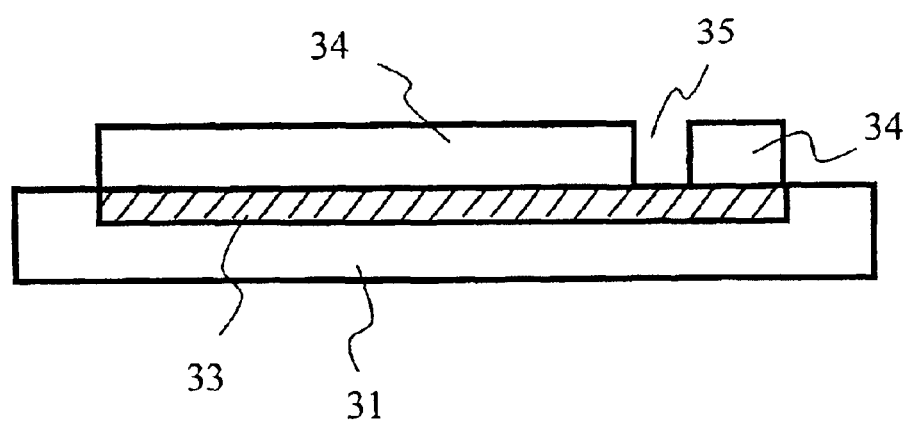

Each of FIGS. 3A and 3B shows another constitutional example of an electrophoresis chip of the invention. FIG. 3A is a plan view; and FIG. 3B is a sectional view taken along a line A–A'.

The electrophoresis chip of the embodiment is different from that of the first embodiment in that a gap 35 for receiving sample solution is formed in a part of an electrophoresis gel (electrophoresis lane). The gap 35 is formed on a hydrophilic region 33, which is surrounded with a hydrophobic region 32. Thus, when sample solution is dropped to the gap 35, the sample solution is held in the gap 35 formed in the electrophoresis gel 34.

For example, if on the hydrophilic region 33 having a width of 2 mm and a length of 30 mm, a 0.5% agarose gel is formed in a position apart from one end thereof by 10 mm in such a way as to provide a gap of a length of 0.5 mm, the gel is formed to have a thickness of 1.5 mm at the center. The gap 35 can be formed by first installing a polystyrene film having a thickness of 0.5 mm with its end in contact with a substrate 31, and then removing the film after formation of a gel. In both ends of the electrophoresis gel 34, electrodes having structures, for example, shown in FIGS. 2A and 2B, are provided. By performing electrophoresis at an electric field strength of 100 to 200 V/cm, a charged sample in the sample solution added to the gap 35 is moved to the gel 34, and separated.

Figure 4:
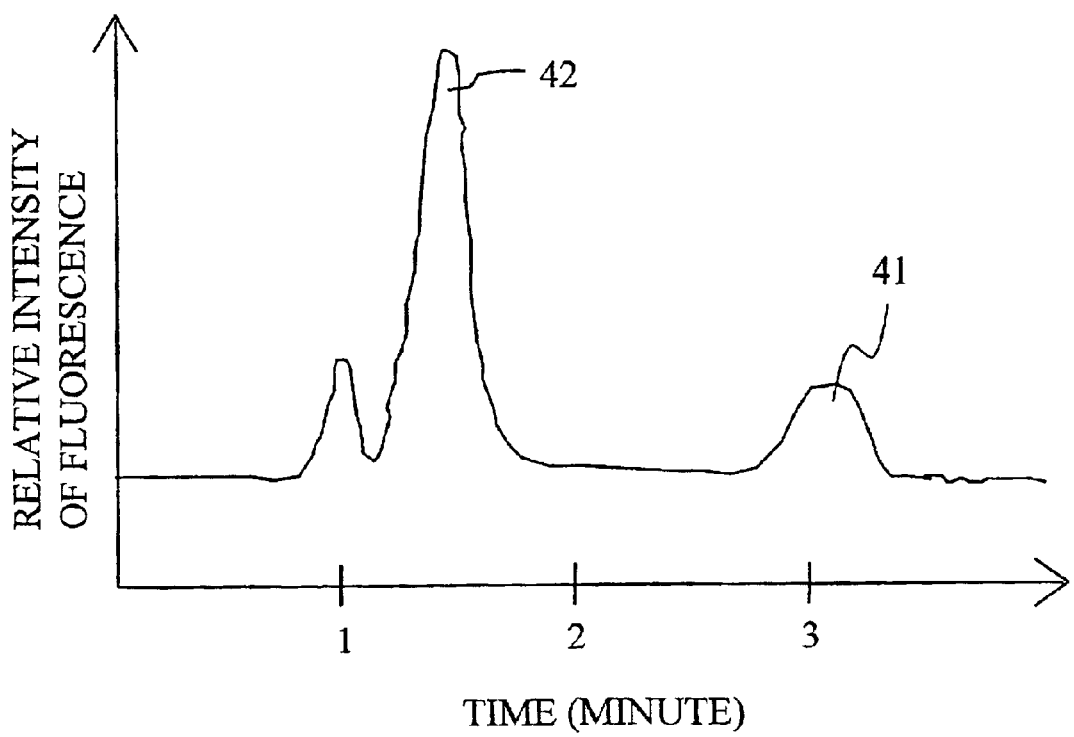
FIG. 4 is a view showing a measuring example of electrophoresis.

Actually, as a sample, a PCR product expected to be made of 1030 bases was produced by using Sulforhodamine 101 fluorescent marked primer and unmarked primer. This sample solution was supplied to the sample holding gap 35 of the electrophoresis chip of the embodiment, a negative electrode was fixed to an end of the electrophoresis gel 34 close to the sample holding gap 35, a positive electrode to an end away from the same, and electrophoresis was carried out at a electric field strength of 100 V/cm. A position apart from a tail end of the electrophoresis gel away from the sample holding gap 35 by 10 mm was irradiated with an excitation light from an He—Ne (594 nm) laser, and a change with time in a fluorescence of 615 nm to 625 nm was measured by a spectroscope. A result of the measurement is shown in FIG. 4. As can be understood from FIG. 4, analysis can be completed within about 3 min., by using the electrophoresis chip of the embodiment. A peak 41 is expected to be a PCR product of 1030 bases, and a peak 42 is possibly unreacted fluorescent marked primer.

[Third Embodiment]

Figure 5A:
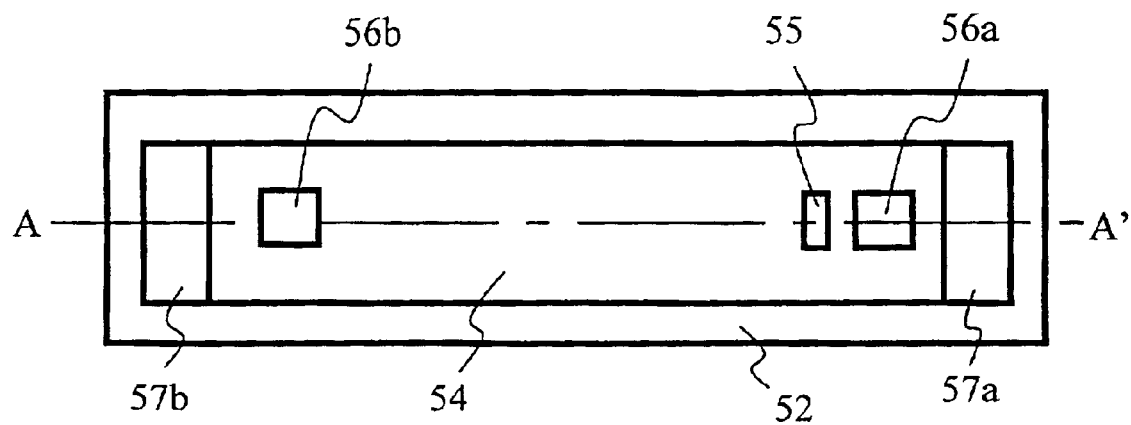
FIGS. 5A and 5B are explanatory views, each thereof showing another constitutional example of an electrophoresis chip according to the invention.
Figure 5B:
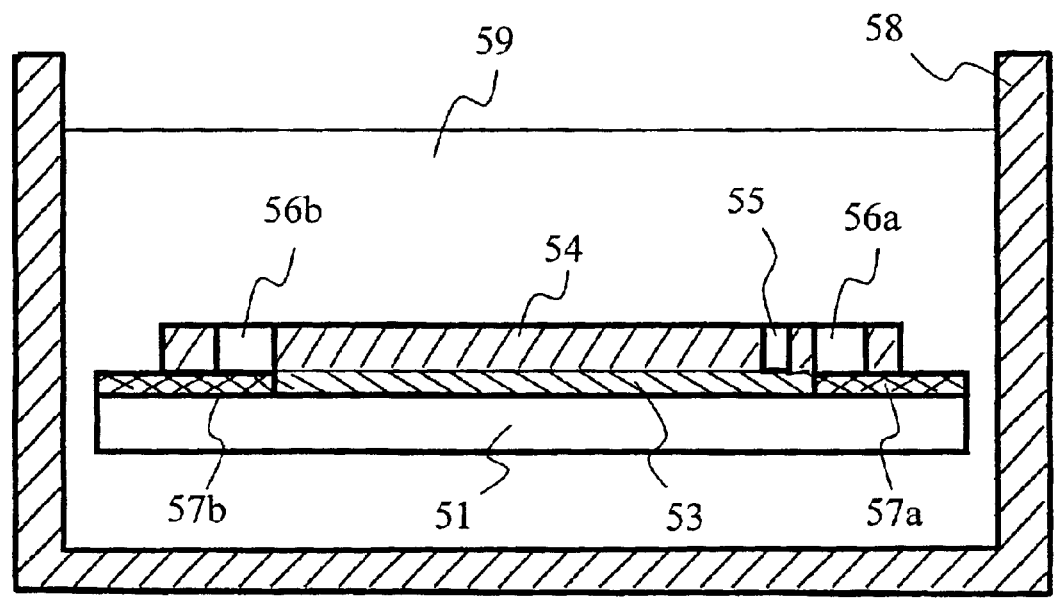

FIGS. 5A and 5B are explanatory views, each thereof showing another constitutional example of an electrophoresis chip according to the invention: FIG. 5A being a plan view; and FIG. 5B being a sectional view taken along a line A–A'.

The electrophoresis chip of the embodiment is constructed in a manner that a hydrophobic region 52 and a hydrophilic region 53 are formed on a surface of a substrate 51, and an electrophoresis gel 54 is formed on the hydrophilic regions 53. The electrophoresis gel (electrophoresis lane) 54 includes a sample well 55 formed to receive sample solution, and buffer solution wells 56a and 56b formed to receive electrophoresis buffer solution. Platinum electrodes 57a and 57b are formed on the substrate 51, and the buffer solution wells 56a and 56b are formed on the platinum electrodes 57a and 57b so as to expose the platinum electrodes 57a and 57b to well bottom portions. The sample well 55 is formed in a position close to one buffer solution well 56a between the two buffer solution wells 56a and 56b.

The electrophoresis gel 54 having the sample well 55 and the buffer solution wells 56a and 56b can be formed, for example, in the following manners that: on the hydrophilic region 53 having a width of 5 mm and a length of 100 mm, a thin pin of 2×1 mm in section is put up at a position apart from one end of the gel by 10 mm, and on the platinum electrodes 57a and 57b having widths of 5 mm continuous from both sides of the hydrophilic region 53, two thin pins of 2×5 mm in section are put up at positions apart from respective ends of the gel by 5 mm; and the pins are removed after forming the gel. The pin may be made of, for example, stainless steel.

Electrophoresis buffer solution is held in the buffer solution wells 56a and 56b, a sample of 1 micro-liter is added to the sample well 55, and then the entire electrophoresis chip is dipped in hydrophobic mineral oil 59 having been filled a container 58. In this example, the buffer solution held in the buffer solution wells 56a and 56b, and the sample solution held in the sample well 55 are disposed inside a space three-dimensionally plotted by the wells formed in the electrophoresis gel 54 and hydrophobic solution 59. Thus, evaporation or drying of the sample solution and the buffer solution can be prevented. The buffer solution in the buffer solution wells 56a and 56b serves as electrode solution for keeping pH constant.

By bringing lead wires into contact with the platinum electrodes 57a and 57b installed in both sides of the electrophoresis gel 54, a sample component can be subjected to electrophoresis separation as in the case of the second embodiment. Here, the mineral oil lighter in specific gravity than the buffer solution was used to prevent the evaporation of moisture contained in the gel or the sample. However, if a fluorocarbon or the like heavier in specific gravity than the buffer solution is used to prevent evaporation, the electrophoresis chip shown in FIGS. 5A and 5B should be reversed upside down, and dipped in drying prevention solution 59 with the electrophoresis surface down. A requirement of the drying prevention solution to be used here is that it is electrically nonconductive and not dehydrated.

[Fourth Embodiment]

Figure 6A:
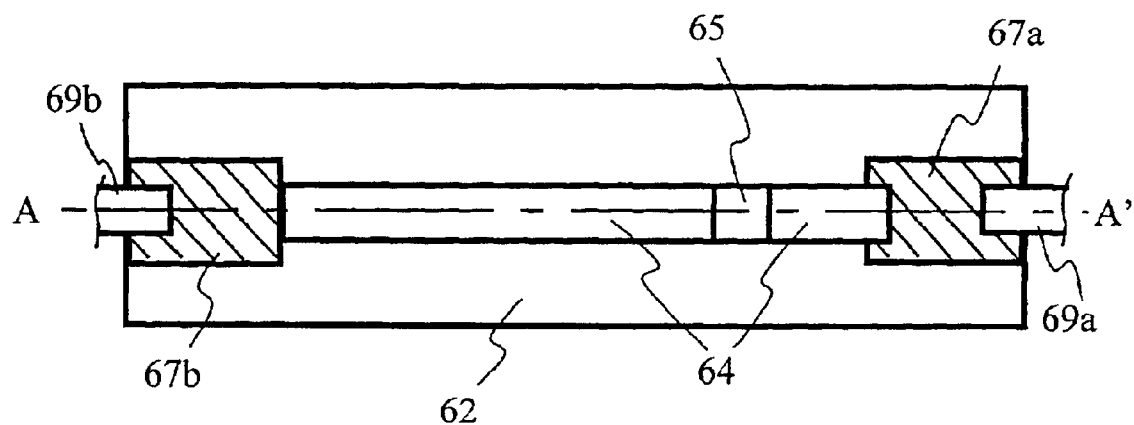
FIGS. 6A and 6B are explanatory views, each thereof showing another constitutional example of an electrophoresis chip according to the invention.
Figure 6B:
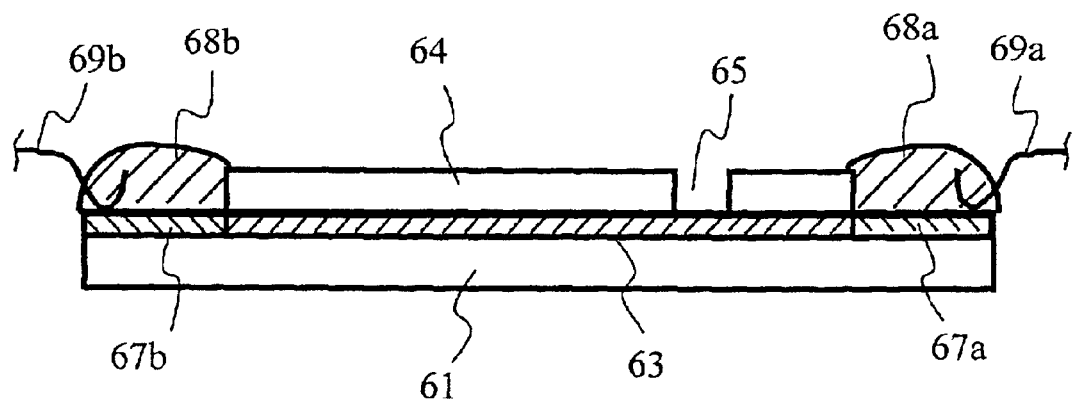

FIGS. 6A and 6B are explanatory views, each thereof showing another constitutional example of an electrophoresis chip according to the invention: FIG. 6A being a plan view; and FIG. 6B being a sectional view taken along a line A–A'.

The electrophoresis chip of the embodiment has a structure of an electrophoresis gel having a sample holding gap similar to that of the electrophoresis chip described above with reference to FIGS. 3A and 3B, but a structure of an electrode portion is different. A hydrophobic region 62, a hydrophilic region 63, and electrodes 67a and 67b are formed on a surface of a substrate 61 beforehand. The electrodes 67a and 67b are made of platinum thin films, and substantially hydrophilic. The thin and long linear hydrophilic region 63 and the electrodes 67a and 67b are surrounded with the hydrophobic region 62. In other words, a region other than the hydrophilic region is a hydrophobic region.

This electrophoresis chip was produced in the following manner. First, surfaces of the electrodes 67a and 67b and a portion equivalent to a gap 65 were taped by a polyimide tape, and acrylamide monomer (T=7% and C=5%) and gel precursor containing ammonium persulfate and TEMED as polymerization initiators were dropped to the hydrophilic region 63. Then, the precursor solution was adhered to the hydrophilic region 63. Subsequently, the substrate 61 was immediately placed in a box filled with nitrogen gas, and polymerized for 30 min. After the polymerization, the tape was removed. By such a series of operations, a polyacrylamide gel 64 is formed in the hydrophilic region 63 of the surface of the substrate by being divided by the gap 65. In this state, the entire electrophoresis chip can be rinsed in solution containing glycerin of 3%, dried and held. In use, the electrophoresis chip can be used by being rinsed in 1×TBE for 5 min.

In the foregoing, the polyacrylamide gel was used as the electrophoresis medium. However, a similar electrophoresis chip can be produced by using an agarose gel. Lead wires 69a and 69b are installed on the electrodes 67a and 67b, and electrode solutions (1×TBE) 68a and 68b of 10 micro-liters are added to contact portions between the electrodes and the lead wires. FIG. 6B shows a state in which the electrode solutions 68a and 68b are held on the electrodes 67a and 67b. The electrode solution serves to keep pH constant. By employing such an electrode structure, attaching of the electrodes is facilitated, and an operation is facilitated. Thus, an electric field can be surely applied. Moreover, by the electrode solution, a pH change near the electrode can be limited to a minimum. For long-time electrophoresis, the electrode solution can be replaced or a new one can be added in the midway.

Figure 7A:
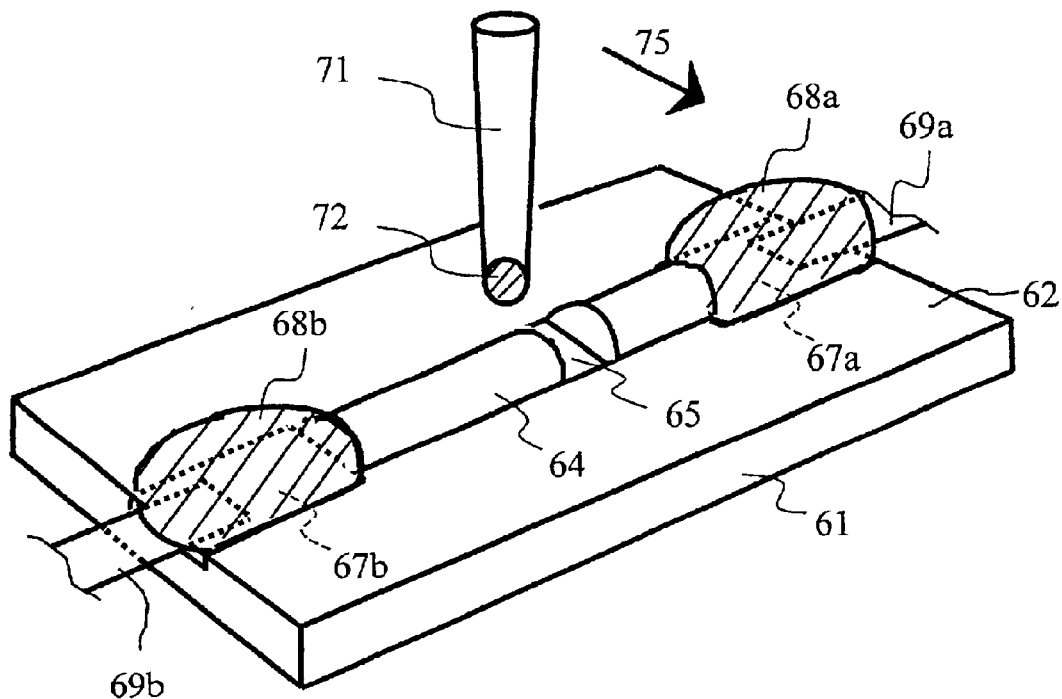
FIGS. 7A and 7B are perspective views, each thereof showing a method of supplying a sample to the electrophoresis chip shown in FIGS. 6A and 6B.
Figure 7B:
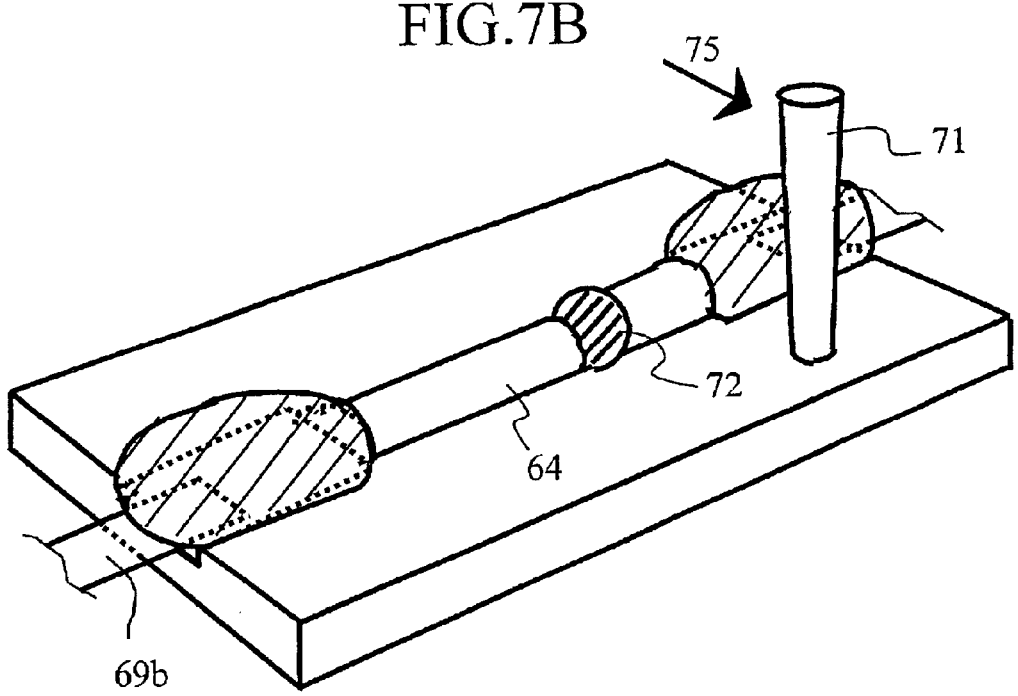

FIGS. 7A and 7B are perspective views, each thereof showing a method in which a sample is supplied to the electrophoresis chip, shown in FIGS. 6A and 6B, and held therein. As shown in FIG. 7A, a sample droplet 72 is adhered to a tip of a needle 71 having a diameter of 0.4 mm, the tip thereof being hydrophilic, and a side face thereof hydrophobic. In this case, a volume of the droplet 72 is about 500 nL. The droplet 72 is moved in a direction of an arrow 75 to pass through the gap 65 as a hydrophilic region in contact with the hydrophobic region 62 of the substrate 61. A space of the gap is about 0.5 mm.

When the tip of the needle 71 is passed through the gap 65, the droplet 72 adhered to the tip of the needle 71 is, as shown in FIG. 7B, captured in a form of burying the gap 65 of the electrophoresis gel 64, and thus the electrophoresis gel 64 is connected. Thus, a very small quantity of a sample can be supplied to the gap 65 of the electrophoresis gel 64 and held. Electrophoresis is started when an electric field is applied through lead wires 69a and 69b to the electrodes 67a and 67b, a movement of a charged material in the sample solution is started. The electrode solutions 68a and 68b serve to connect the lead wires 69a and 69b with the electrodes 67a and 67b by low resistance.

Hereinafter, description is made of a specified measuring example using the electrophoresis chip of the embodiment. Here, a restriction enzyme fragment of an unknown DNA is prepared, and measured by using a polyacrylamide gel. A result of the measurement is described.

A sample was prepared in the following manner. As a model sample, a DNA fragment mixture was prepared by cutting a human originated unknown sequence DNA clone of 2.1 k bases with restriction enzyme and connecting an adapter sequence to a 3' end. This DNA of 2.1 kb was cut by restriction enzyme Hsp92II, and a known-sequence adapter was connected to both 3' ends by DNA ligase. That is, a cut DNA of 400 fmol was dissolved in 10 mM Tris-HCl (pH 7.4) containing 10 mM $MgCl_2$, and 15 mM KCl, and completely cut by adding Hsp92II (Promega, UK) of 40 units, and reacting it at 37° C. for 2 hours. After the DNA was recovered by ethanol precipitation, a phosphate group at a 5' end was removed by alkaline phosphatase. An adapter 5'-pACTGGCCGTCGTTT-SR101-3' (20 pmol) marked at a 3' end by phosphor Sulforhodamine 101 (SR101) and helper oligomer 5'-AAACGACGGCCAGTCATGp-3' (20 pmol) were added to a cut DNA fragment mixture of 400 fmol to prepare 40 micro-liters, Ligation High (TOYOBO) of 20 micro-liter was added, and 1-hour ligation reaction was carried out at 16° C. Thus, an adapter sequence ACTGGCCGTCGTTT-SR101 was introduced only to the 3' end of each DNA, and simultaneously each fragment was marked by phosphor Sulforhodamine 101. The Lygation reaction is a reaction for connecting a phosphate group of the DNA 5' end and OH of the 3' end. By such a method, since the 5' end of helper oligomer is modified by the phosphate group, ligation between the adapters can be suppressed. Moreover, since the phosphate group of the 5' end of the DNA fragment is removed, recombination of DNA fragments can be prevented. Therefore, the adapters was surely introduced.

Figure 8:
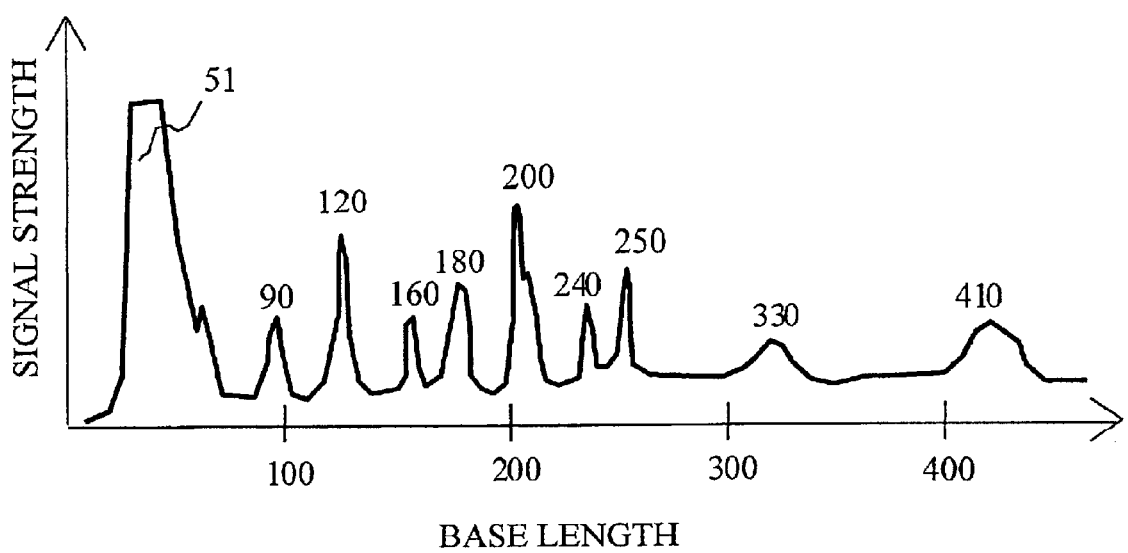
FIG. 8 is a view showing a measuring example of electrophoresis.

Detection of a DNA fragment by the electrophoresis chip of the embodiment was carried out in the following manner. By the method described above with reference to FIGS. 7A and 7B, sample solution of 1 micro-liter was held in the sample holding gap 65 of the electrophoresis chip. The electrodes 67b and 67a shown in FIGS. 6A and 6B were set respectively as positive and negative electrodes, and a sample DNA was moved into the gel by applying an electric field of 20 V/cm for 10 sec. Then, the electric field was increased to 100 V/cm, and the electrophoresis was continued more. A position of 1 cm from an end surface of the electrophoresis gel away from the sample holding gap 65 was continuously irradiated with an excitation light emitted from the He—Ne laser of 594 nm to monitor fluorescence. An emitted fluorescence was divided by a diffraction grating, and a light of 615 nm to 625 nm was measured by a high-sensitivity cooling CCD camera. As a result, an electrophoresis band like that shown in FIG. 8 was obtained. A DNA length of an abscissa is a value obtained beforehand by measurement with Gene Scan Locks 500 of Applied Biosystems Inc. as a marker under the same conditions. A large electrophoresis separation band around 50 base length represents unreacted primer. A total of base lengths of other bands is about 2000 bases, which coincides with a length of about 2.1 k base of the sample DNA.

[Fifth Embodiment]

Figure 9A:
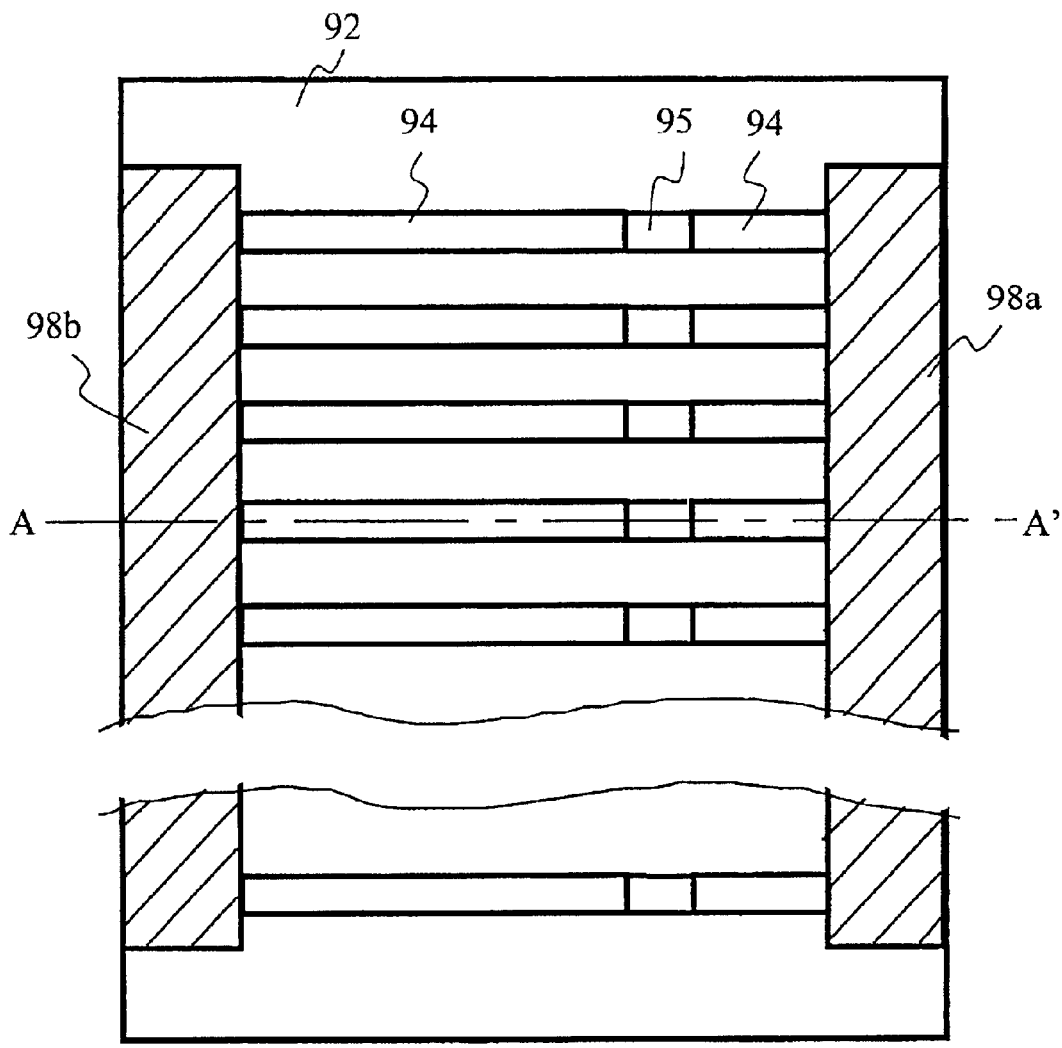
FIGS. 9A and 9B are explanatory views, each thereof showing another constitutional example of an electrophoresis chip according to the invention.
Figure 9B:
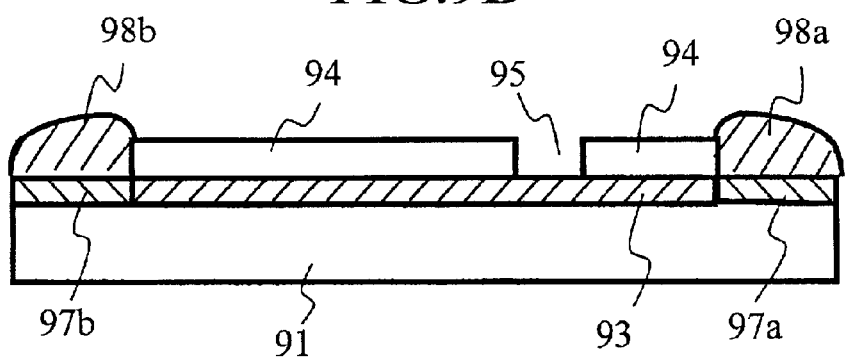

FIGS. 9A and 9B are explanatory views, each thereof showing another constitutional example of an electrophoresis chip according to the present invention: FIG. 9A being a plan view; and FIG. 9B is a sectional view taken along a line A–A'.

The electrophoresis chip of the present embodiment is formed in a manner that a plurality of thin and long linear hydrophilic regions 93 are formed approximately in parallel with each other on a substrate 91. An electrophoresis gel 94 is formed on each of the hydrophilic regions 93. The hydrophilic region 93 is surrounded with a hydrophobic region 92. Each of the interval between the hydrophilic regions 93 is 4.5 mm. The hydrophilic region has a length of 50 mm, and a width of 1 mm, and has a portion apart from the end by 10 mm, where a gap 95 for adding sample solution is formed. In both ends of each hydrophilic region 93, electrodes respectively as negative and positive 97a and 97b are formed. The negative electrodes 97a are common among all the hydrophilic regions, and the positive electrodes 97b are also common among all the hydrophilic regions. Electrode solutions 98a and 98b are added to the electrodes 97a and 97b to keep pH constant. The gap 95 for adding sample solution has a structure similar to that of described above with reference to FIGS. 6A and 6B, and FIGS. 7A and 7B.

Now, an actual preparation method of an electrophoresis gel is described by taking an example of agarose gel. Agarose is added to buffer solution of 0.5×TAE, and heated to be dissolved by a microwave oven to obtain 0.5% solution. Then, the solution is cooled to 60° C., and the dissolved agarose solution is dropped to a surface of the substrate 91 similarly heated to 60° C. Then, a glass plate is immediately erected to remove excessive agarose solution. By this operation, the agarose solution is removed from the hydrophobic region 92. However, the agarose solution is left in the hydrophilic region 93. Needless to say, the portion corresponding to the sample holding gap 95 and the electrodes 97a and 97b, are masked by a tape to prevent adhesion of agarose. Then, the substrate is placed in a moist box, and cooled at a room temperature for 15 min., thus forming an electrophoresis gel 94. Lastly, the mask is peeled off to form a gap 95 in the electrophoresis gel 94, thus exposing the electrodes 97a and 97b.

Figure 10A:
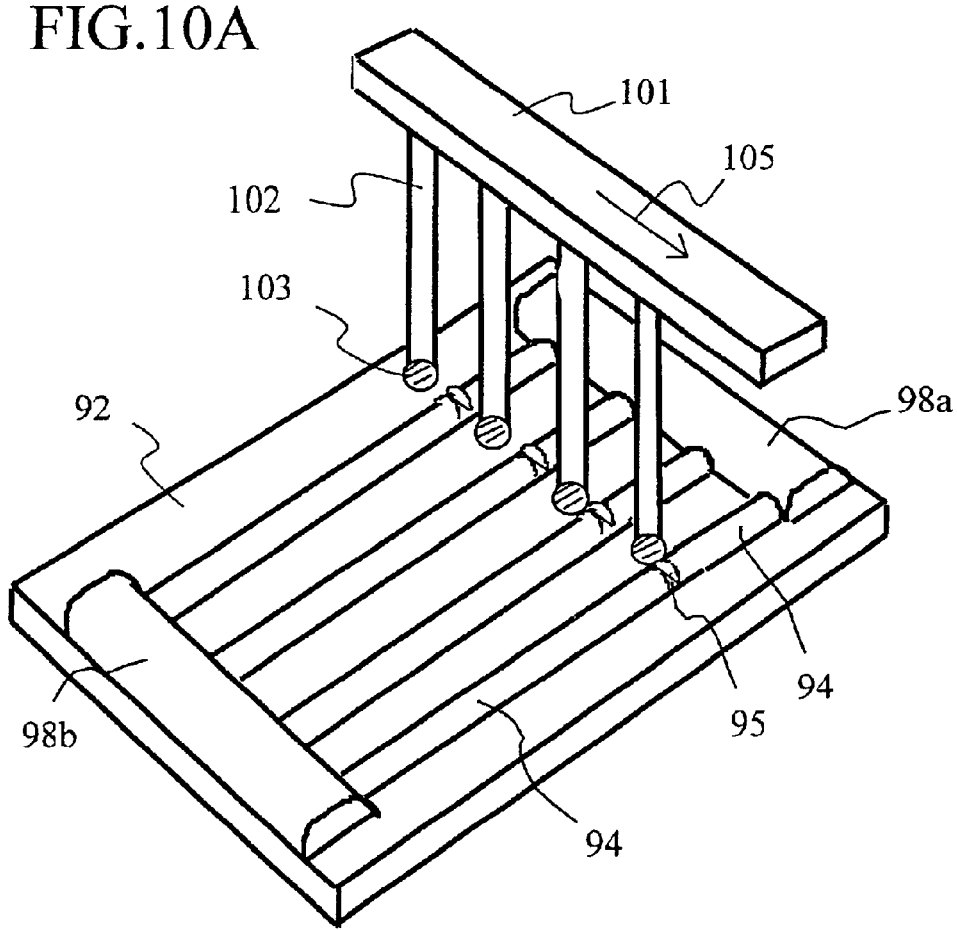
FIGS. 10A and 10B are perspective views, each thereof showing an example of a method of supplying a sample to the electrophoresis chip.
Figure 10B:
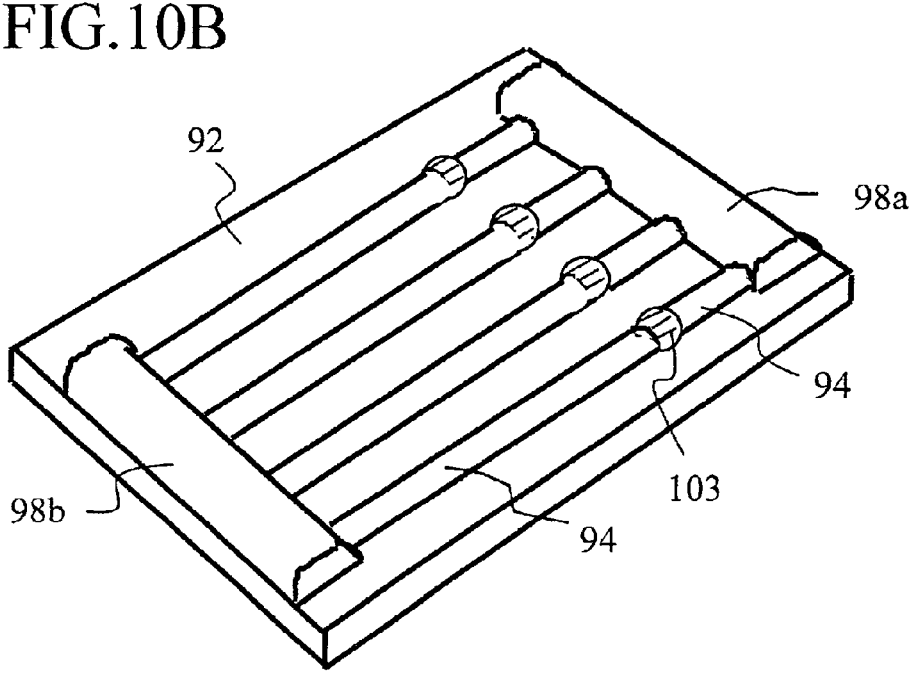
Figure 11:
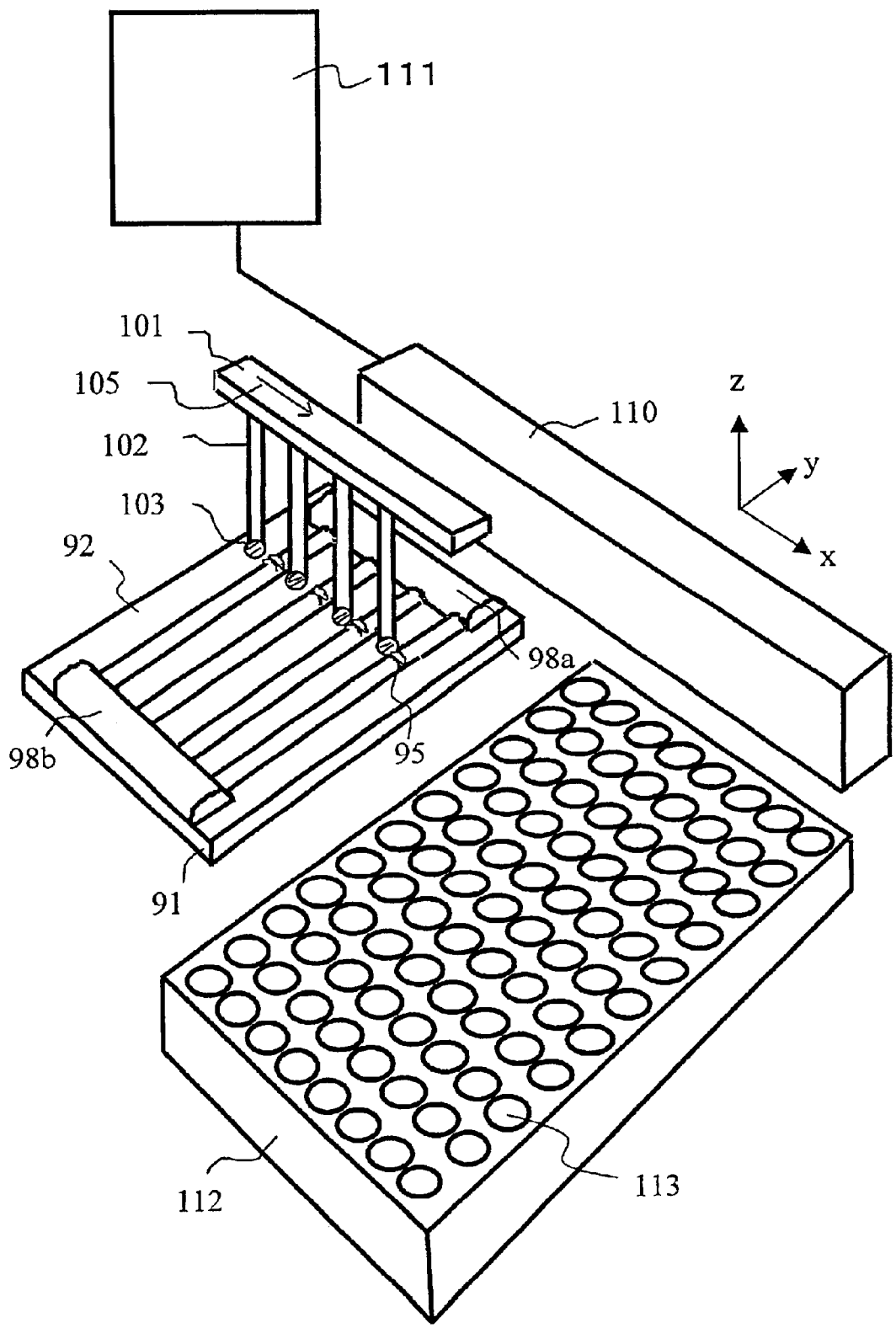
FIG. 11 is a perspective view showing an example of a method of supplying a sample to the electrophoresis chip.

FIGS. 10A and 10B, and FIG. 11 are perspective views, each thereof showing a method of supplying a sample to the electrophoresis chip shown in FIGS. 9A and 9B. Needles 102 for holding sample solution are attached to a stage 101 by a number equal to that of electrophoresis lanes. A space between adjacent needles 102 is set equal to, for example, a pitch of holes in 96-hole type microplate. A pitch between the needles is equivalent to a pitch between a plurality of electrophoresis gels 94, i.e., 9 mm or 4.5 mm. The sample solution is supplied by the micro-plate of 96 holes 112 shown in FIG. 11 or a micro-plate of a 384-hole type. Here, the micro-plate of a 96-hole type is used.

The stage 101 having the needle 102 fixed is attached to a driving device 110 for moving the stage in a direction of an x axis, and a direction of a z axis perpendicular to the x axis. The driving device 110 uses a stepping motor as a driving source, and is controlled by a control unit 111. First, by a signal from the control unit 111, the driving device 110 is moved in the direction of the z axis as approaching the micro-plate. A needle array is dipped in continuous holes 113 of the micro-plate 112, and the sample solution is adhered to a tip of each needle 102. A tip of the needle 102 is made hydrophilic, and its side face hydrophobic. Accordingly, a specific quantity of solution can be held in the needle tip if surface tension is constant. When analysis of more precise solution quantity is necessary, instead of the needle, for example, a capillary having an inner diameter 50 $\mu$m and an outer diameter of 200 $\mu$m may be used instead of the needle, for sucking the sample solution and a constant quantity thereof, and a constant quantity is injected in a divided manner. Then, by a signal from the control unit 111, the driving device 110 is moved in the direction of the z axis to be away from the micro-plate 112. Subsequently, the driving device 110 is moved in the direction of the x axis to move the needle above the substrate 61. By a signal from the control unit 111, the driving device 110 is moved in the direction of the z axis to bring a droplet 103 adhered to the tip of the needle 102 into contact with the hydrophobic region 92 of the substrate 91.

Subsequently, as described above with reference to FIGS. 7A and 7B, the driving device 110 is moved by a signal from the control unit 111, so that the needle (tip diameter 0.2 mm) 102 having the sample droplet 103 adhered to the tip is moved in the direction of a arrow 105 so as to pass through a gap 95 as the hydrophilic region 93 in contact with the hydrophilic region 92. A space between the gaps 95 is about 0.3 mm. When the tip of the needle 102 is passed through the gap 95, the droplet 103 adhered to the tip of the needle 102 is captured by the gap 95 in a form of burying the gap 95 of the electrophoresis gel 94 and, as shown in FIG. 10B, the separated electrophoresis gel 94 is connected by the gap 95.

Then, with the electrodes 97a and 97b respectively set as negative and positive electrodes, electrophoresis is started by applying an electric field between the electrodes, and a movement of a charged material in the sample solution is started. By performing electrophoresis with an electric field strength of 100 to 200V/cm, the charged sample in the sample solution added to the gap 95 is moved to the electrophoresis gel 94, and separated.

By adding ethidium humidifier or the like, which is a fluorescent intercalator to the electrophoresis gel 94 or the electrode solution 98*a* beforehand, the ethidium humidifier is intercalated to a double stranded DNA in electrophoresis. A laser beam from YAG laser is irradiated onto the position apart from a tail end of the electrophoresis gel by 10 mm away from the sample holding gap 95, and a fluorescent signal from an electrophoresis separation band of the double stranded DNA is traced with time, whereby an electrophoresis pattern can be obtained.

[Sixth Embodiment]

Figure 12A:
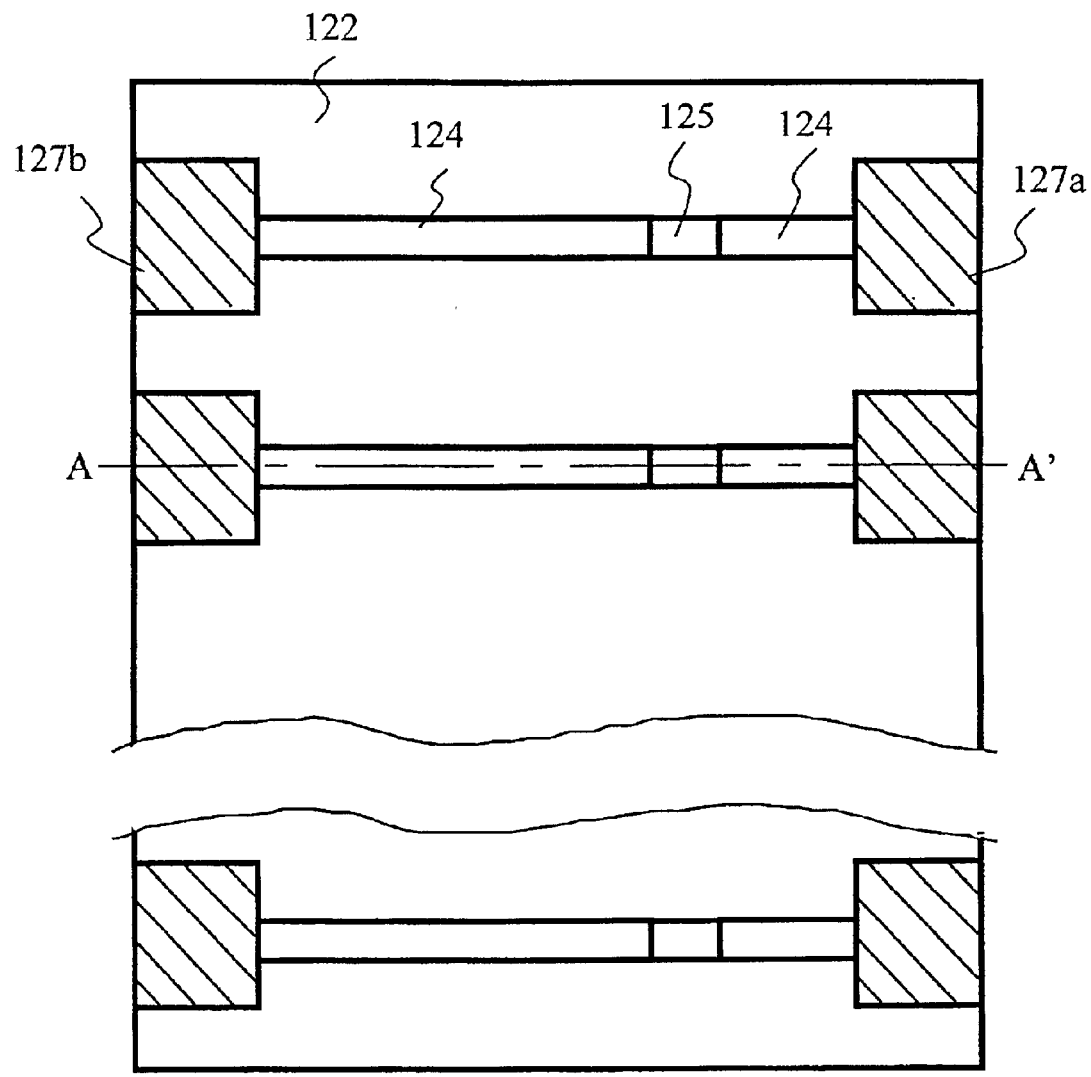
FIGS. 12A and 12B are explanatory views, each thereof showing another constitutional example of an electrophoresis chip according to the invention.
Figure 12B:
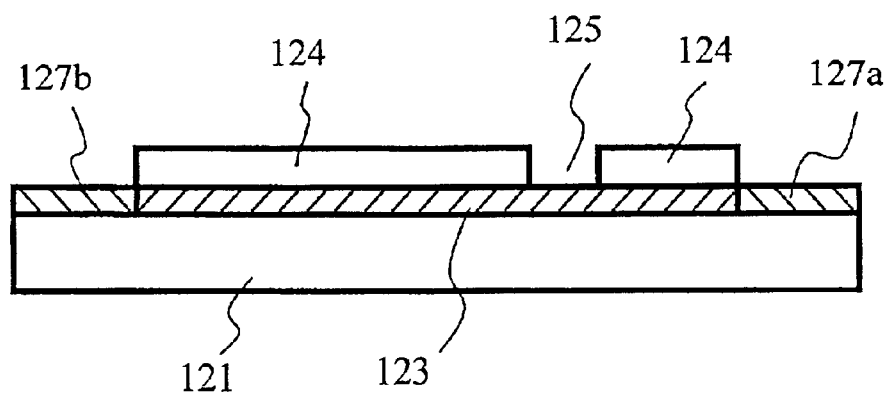

FIGS. 12A and 12B are explanatory views, each thereof showing another constitutional example of an electrophoresis chip according to the present invention: FIG. 12A being a plan view; and FIG. 12B is a sectional view taken along a line A–A'.

In the electrophoresis chip of the fifth embodiment, common electrodes were formed corresponding to the respective hydrophilic regions. However, in the electrophoresis chip of the present embodiment, individual electrodes (positive and negative electrodes 127*b* and 127*a*) are formed in respective hydrophilic regions 123. Constructions other than the electrode portion are similar to those of the fifth embodiment. That is, the electrophoresis chip of the present embodiment is constructed in a manner that a plurality of thin and long linear hydrophilic regions 123 are formed in parallel with each other on a substrate 121, and an electrophoresis gel 124 is formed on each of the hydrophilic regions 123. The hydrophilic region 123 is surrounded with a hydrophobic region 122. In the electrophoresis gel 124, a gap 125 for adding sample solution is formed in a position close to the negative electrode 127*a*.

The electrophoresis chip of the embodiment is advantageous in that voltage applied to each electrophoresis lane (electrophoresis gel 124) can be individually controlled. That is, in electrophoresis, an electrophoresis speed may slightly vary in each lane. This variance occurs because it is difficult to completely in the same conditions among gels. In most cases, a gel sectional area slightly varies. Thus, if low-voltage electrophoresis is carried out, generated Joule heat may be different, causing a change in an electrophoresis speed of a sample DNA in each gel. In such a case, without placing any samples beforehand, preparatory electrophoresis (prerun) may be carried out to measure a current flowing through each electrophoresis lane, and a voltage may be set for each lane such that an electrophoresis speed of a particular DNA can be constant on each electrophoresis lane. Alternatively, a known DNA is added as a marker to electrophoresis sample solution, and a voltage applied among each lane may be corrected while monitoring an electrophoresis speed of this known DNA.

[Seventh Embodiment]

Figure 13A:
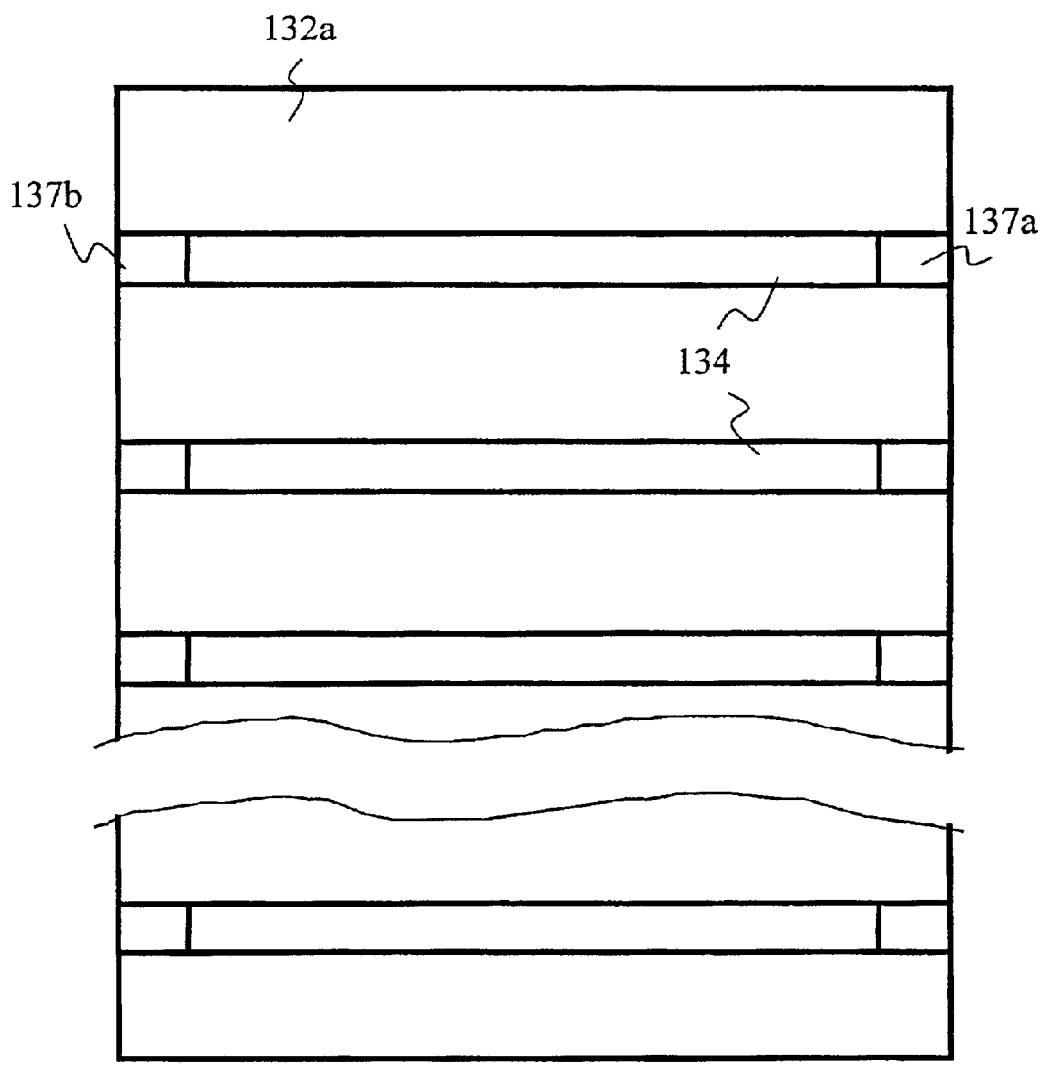
FIGS. 13A and 13B are explanatory views, each thereof showing another constitutional example of an electrophoresis chip of the invention.
Figure 13B:
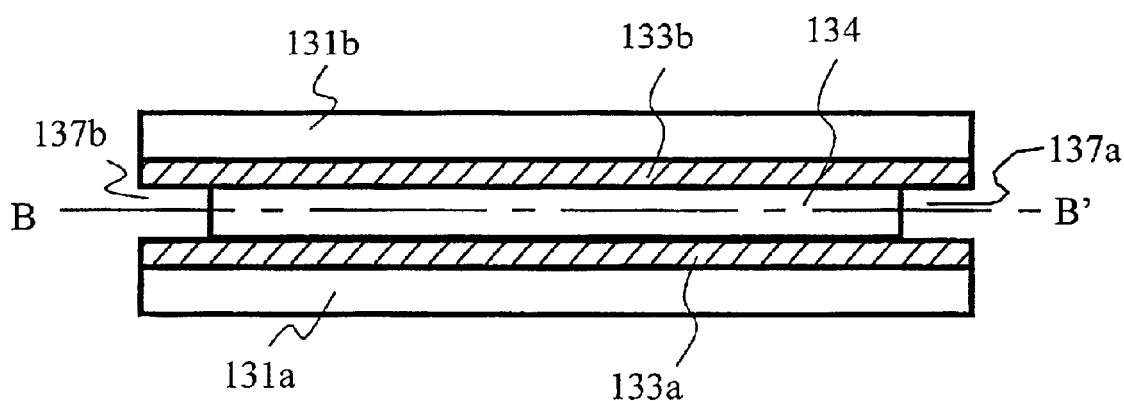

FIGS. 13A and 13B are explanatory views, each thereof showing another constitutional example of an electrophoresis chip according to the present invention: FIG. 13A being a sectional view, in which a center of an electrophoresis chip is cut by a plane parallel to a substrate; and FIG. 13B a sectional view perpendicular to the substrate of the electrophoresis chip; and FIG. 13A is a sectional view taken along a line B–B' of the FIG. 13B.

The electrophoresis chip of the present embodiment is formed in a manner that an electrophoresis gel is formed between hydrophilic regions formed on a surface of two substrates. That is, a plurality of thin and long linear hydrophilic regions 133*a* and 133*b*, and a plurality of hydrophobic regions 132*a* and 132*b* (hydrophobic region 132*b* is located in a substrate 131*b*, not shown) are formed in opposing surfaces of two opposing substrates 131*a* and 131*b* so as to be plane-symmetrical, and an electrophoresis medium (electrophoresis lane 134) is held between the opposing hydrophilic regions 133*a* and 133*b* of the two substrates spaced from each other by a specified gap in parallel. By this electrophoresis chip, an electrophoresis gel 134, a space (space in which the hydrophobic regions of the two substrates face each other), an electrophoresis gel 134, a space, . . . , are repeatedly formed. Thus, an area of the electrophoresis gel 134 exposed to the atmosphere can be reduced, effectively preventing from drying of the electrophoresis gel.

This electrophoresis chip can be produced by first adding gel precursor solution to a gap between the substrates 131*a* and 131*b* disposed at a fixed interval through a spacer, and then removing excessive solution. Alternatively, gel precursor solution is dropped to one substrate 131*a* and, only by loading the other substrate 131*b* through the spacer while the gel precursor solution is held only in the hydrophilic region 133*a*, an electrophoresis lane is automatically formed in a portion held between the hydrophilic regions 133*a* and 133*b* of the two substrates 131*a* and 131*b*. If the latter production method is employed, a foil-layer electrophoresis lane having a spacer thickness set in a range of 0.05 to 0.1 mm can be formed. For use, sample solution is added to one slit for holding both sample solution and electrode solution 137*a*, and a platinum electrode is inserted. The other slit for holding electrode solution 137*b* is filled with the electrode solution, and an electric field is applied with the slits 137*a* and 137*b* to set respectively as negative and positive electrodes. After the application of the electric field for 10 seconds, the slits 137*a* and 137*b* are replenished with new electrode solution. A porous sponge may be contact with the slits for replenishing the electrode solution. Thereafter, in the cases of the other foregoing embodiments, an electrophoresis separation band can be detected. The electrophoresis chip of the present embodiment is advantageous in that a gel having a constant thickness can be formed. Moreover, since the two surfaces are covered with the substrates, prevention of drying in electrophoresis is facilitated.

Figure 14A:
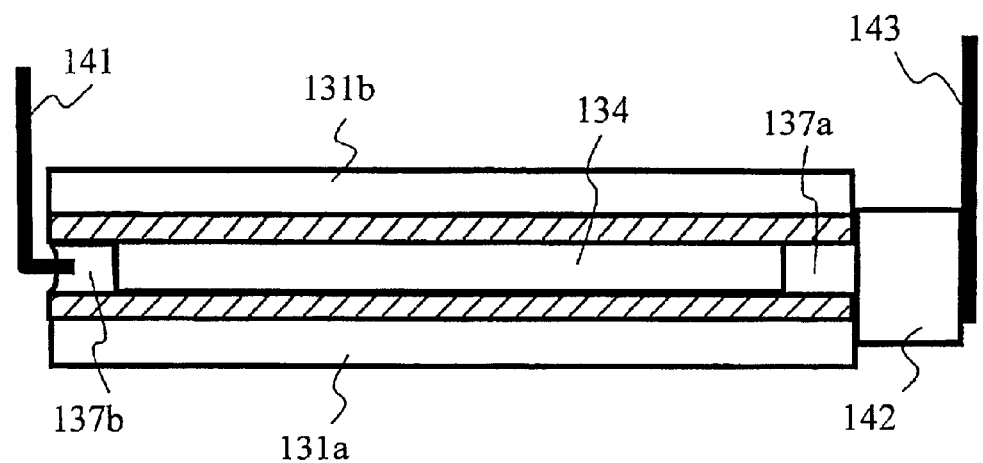
FIGS. 14A and 14B are explanatory views, each thereof showing disposition of electrodes.
Figure 14B:
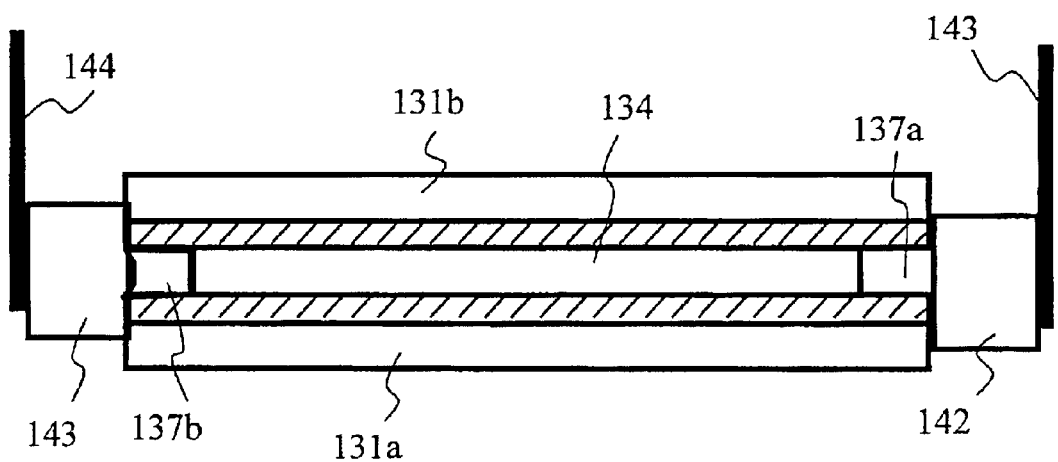

The electrophoresis chip of the present embodiment, as the upper and lower portions of the electrophoresis gel 134 are held between the substrates 131*a* and 131*b*, disposition of electrodes is different from those of the other embodiments. FIGS. 14A and 14B are explanatory views, each thereof showing disposition of electrodes of the present embodiment. First, as shown in FIG. 14A, sample solution is added to the gap 137*b* by a capillary phenomenon, and then a negative electrode 141 is inserted into the gap 137*b*. In a positive electrode side, the gap 137*a* is filled with buffer solution, then a buffer solution holding carrier 142 made of porous plastic or filter paper soaked with the buffer solution is brought into contact with the positive side, and a positive electrode 142 is brought into contact with same from outside of the buffer solution holding carrier. For example, by applying an electric field between the positive electrode 143 and the negative electrode 141 at 80V for 10 seconds, a DNA in the sample solution is introduced to the electrophoresis gel 134. Then, the negative electrode 141 is removed from the electrophoresis chip and, as shown in FIG. 14B, the buffer solution holding carrier 143 soaked with the buffer solution is inserted into the gap 137*b*. In this case, if the buffer solution of the gap 137*b* is short, replenishment is made. The negative electrode 144 is brought into contact with the outside of the buffer solution holding carrier 143 soaked with the buffer solution, and electrophoresis is continued by applying a voltage of 100V between the electrodes 143 and 144. The buffer solution holding carriers 142 and 143 soaked with the buffer solution are used both ends of the electrophoresis chip, for the purpose of securing sufficient buffer solution, and suppressing pH fluctuation near the electrodes caused by solution electrolysis.

[Eight Embodiment]

The structure of the electrophoresis chip or the method of adding the sample to the chip has mainly been described. Now, description is made of specified examples of an electrophoresis unit and a detection unit of an electrophoresis apparatus using the electrophoresis chip of the embodiment.

Figure 15:
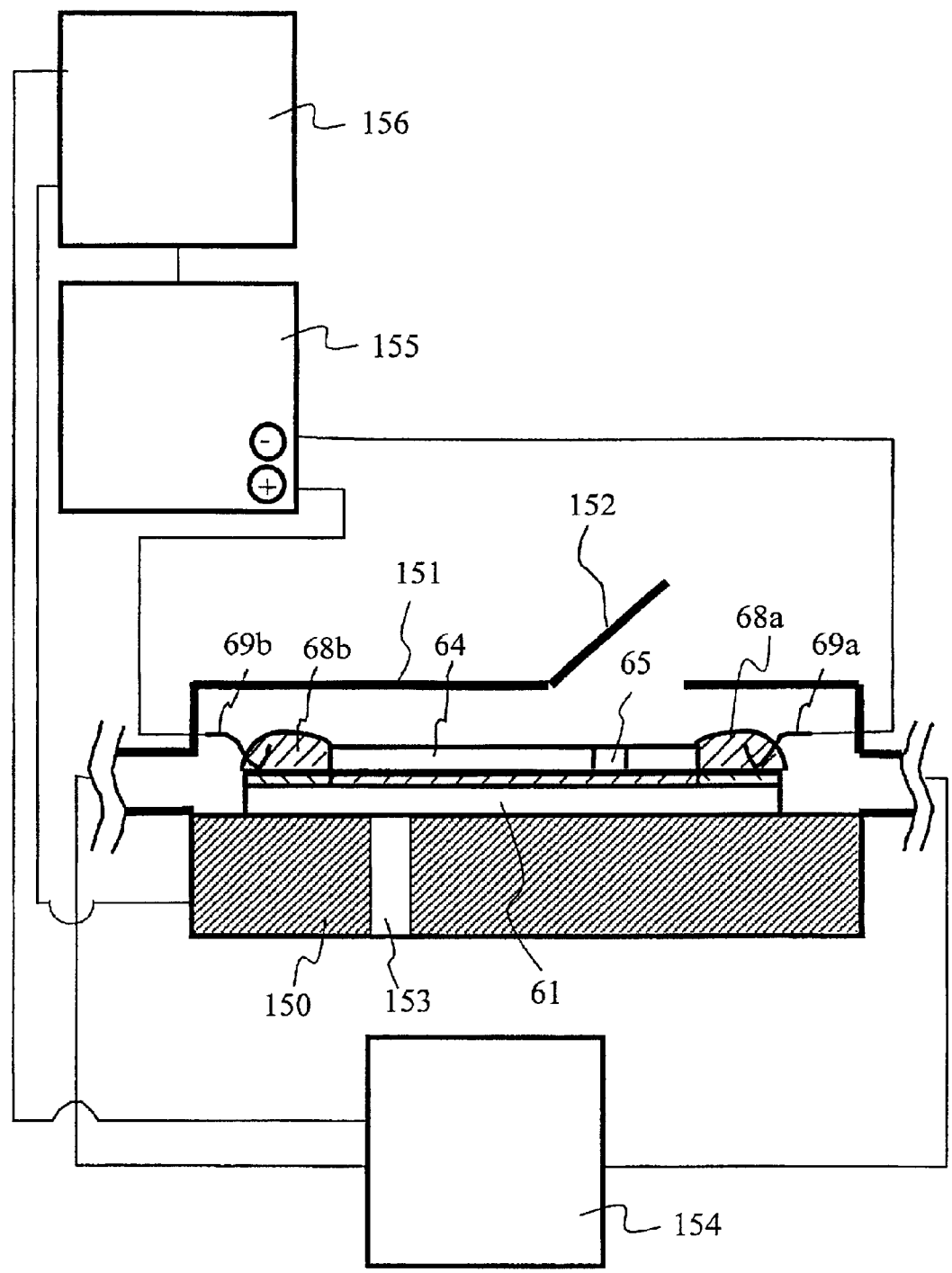
FIG. 15 is a schematic view showing a constitutional example of an electrophoresis apparatus incorporating an electrophoresis chip of the invention.
Figure 16:
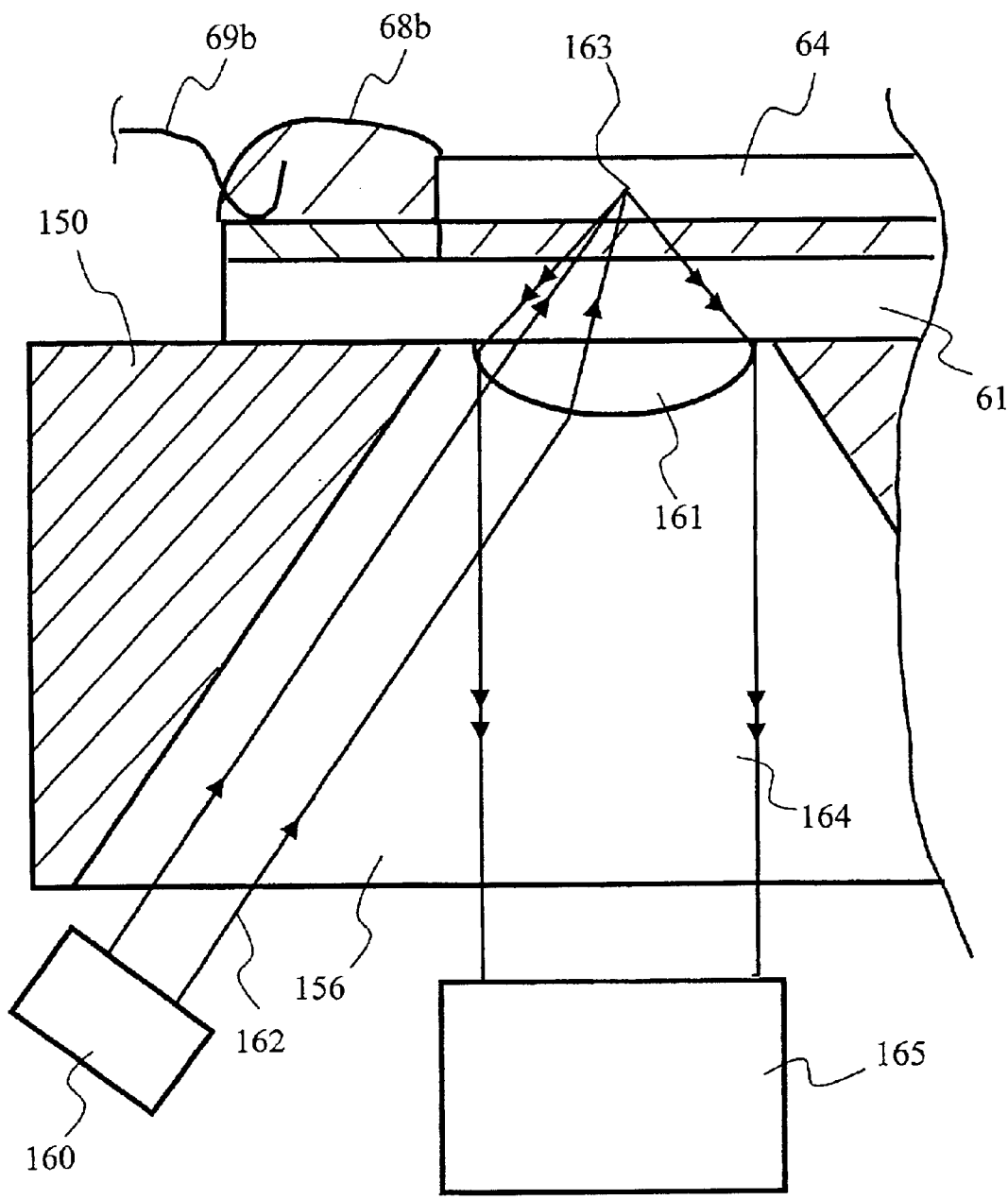
FIG. 16 is an expanded view schematically showing an optical detection unit of the electrophoresis apparatus.

Each of FIGS. 15 and 16 is a schematic view showing a constitutional example of an electrophoresis apparatus incorporating the electrophoresis chip of the fourth embodiment of the present invention shown in FIGS. 6A and 6B. As shown in FIG. 15, the electrophoresis chip includes a substrate 61 loaded on a temperature control unit 150, and the entire chip is housed in a moist box 151. A window 152 is attached to the moist box 151, and a needle for sample supplying can access a sample holding gap 65. A humidifier 154 is attached to the moist box 151. An electrophoresis power source 155 is attached to the electrodes 67a and 67b of the electrophoresis chip. The humidifier 154, the electrophoresis power source 155, and the temperature control unit 150 are connected to a control unit 156. By the control unit 156, temperature/humidity control, and electrophoresis control are carried out. A through-hole 153 is provided in the part of the temperature control unit 150, and an inside of the electrophoresis gel 64 is irradiated with an excimer laser beam for detecting a fluorescence.

FIG. 16 is an enlarged view schematically showing an optical detection unit of the electrophoresis apparatus. In the through-hole 153 provided in the temperature control unit 150, a lens 161 is disposed very close to the substrate 61 of the electrophoresis chip, and a focus 163 of a laser beam 162 emitted from an excimer laser 160 is set on the electrophoresis gel 64. The substrate 61 is irradiated obliquely with the excimer laser beam 162 for the purpose of preventing a reflected light of the substrate surface from being made incident on a detector. A fluorescent marked DNA is moved in the electrophoresis gel 64 and, when a focal region 163 of the excimer laser beam 162 is reached, a fluorescence is emitted therefrom. The fluorescence is radiated in all directions, and only a fluorescence made incident on the lens 161 is detected as a fluorescent beam 164 by a detector 165.

As a representative example, the constitutional example of the electrophoresis apparatus incorporating the electrophoresis chip shown in FIGS. 6A and 6B has been described. However, the electrophoresis chips of the other foregoing embodiments of the present invention can also be used by being incorporated in similarly structured electrophoresis apparatus.

Next, description will be made of the other aspects of the present invention.

(1) An electrophoresis apparatus is provided, comprising an electrophoresis chip. The electrophoresis chip includes: a first hydrophilic region having a predetermined width, and a first length in a longitudinal direction for connecting first and second ends with each other, in which an electrophoresis medium is formed; a second hydrophilic region having a predetermined width, and a second length in the longitudinal direction for connecting first and second ends with each other, in which an electrophoresis medium is formed; a first region, in which a negative electrode is formed to be connected to the first end of the first hydrophilic region; a second region, in which a positive electrode is formed to be connected to the first end of the second hydrophilic region; a third hydrophilic region formed in a region of a gap, in which the second ends of the first and second hydrophilic regions face each other in the longitudinal direction, and adapted to receive a droplet of solution containing a fluorescent marked sample; and a first hydrophobic region surrounding the first region, the first hydrophilic region, the third hydrophilic region, the second region, and the second hydrophilic region. These regions are formed on a surface of an electrical insulating substrate, and an electrophoresis lane is formed by the electrophoresis medium formed in the first hydrophilic region, the droplet supplied to the third hydrophilic region, the electrophoresis medium formed in the second hydrophilic region.

(2) An electrophoresis apparatus is provided, comprising an electrophoresis chip. The electrophoresis chip includes: a first hydrophilic region having a thin and long shape, in which an electrophoresis medium is formed; a second hydrophilic region having a thin and long shape, and formed in a longitudinal direction of the first hydrophilic region, in which an electrophoresis medium is formed; a third hydrophilic region formed in a gap region, in which ends of the first and second hydrophilic regions face each other in the longitudinal direction, and adapted to receive a droplet of solution containing a sample; and a first hydrophobic region surrounding the first hydrophilic region, the third hydrophilic region, and the second hydrophilic region. These regions are formed on a surface of an electrical insulating substrate, and an electrophoresis lane is formed by the electrophoresis medium formed in the first hydrophilic region, the droplet supplied to the third hydrophilic region, the electrophoresis medium formed in the second hydrophilic region.

(3) An electrophoresis apparatus is provided, comprising an electrophoresis chip, a light source and a photodetector. The electrophoresis chip includes: a first hydrophilic region having a predetermined width, and a first length in a longitudinal direction for connecting first and second ends with each other, in which an electrophoresis medium is formed; a second hydrophilic region having a predetermined width, and a second length in the longitudinal direction for connecting first and second ends with each other, in which an electrophoresis medium is formed; a first region, in which a negative electrode is formed to be connected to the first end of the first hydrophilic region; a second region, in which a positive electrode is formed to be connected to the first end of the second hydrophilic region; a third hydrophilic region formed in a region of a gap, in which the second ends of the first and second hydrophilic regions face each other in the longitudinal direction, and adapted to receive a droplet of solution containing a fluorescent marked sample; and a first hydrophobic region surrounding the first region, the first hydrophilic region, the third hydrophilic region, the second region, and the second hydrophilic region. These regions are formed on a surface of an electrical insulating substrate, and an electrophoresis lane is formed by the electrophoresis medium formed in the first hydrophilic region, the droplet supplied to the third hydrophilic region, the electrophoresis medium formed in the second hydrophilic region. In this case, the sample is subjected to electrophoresis separation by applying a voltage between the positive and negative electrodes, a predetermined position of the electrophoresis lane formed in the second region is irradiated with a light emitted from the light source, a fluorescence generated from fluorescent mark is detected by the photodetector, and the sample having been subjected to the electrophoresis separation is detected.

(4) An electrophoresis apparatus is provided, comprising: an electrophoresis chip; a constant temperature and humidity tank, in which an internal temperature and humidity are kept substantially constant, and the electrophoresis chip is disposed; a light source disposed outside of the constant temperature and humidity tank; and a photodetector disposed outside of the constant temperature and humidity tank. The electrophoresis chip includes: a first hydrophilic region having a predetermined width, and a first length in a longitudinal direction for connecting first and second ends with each other, in which an electrophoresis medium is formed; a second hydrophilic region having a predetermined width, and a second length in the longitudinal direction for connecting first and second ends with each other, in which an electrophoresis medium is formed; a first region, in which a negative electrode is formed to be connected to the first end of the first hydrophilic region; a second region, in which a positive electrode is formed to be connected to the first end of the second hydrophilic region; a third hydrophilic region formed in a region of a gap, in which the second ends of the first and second hydrophilic regions face each other in the longitudinal direction, and adapted to receive a droplet of solution containing a fluorescent marked sample; and a first hydrophobic region surrounding the first region, the first hydrophilic region, the third hydrophilic region, the second region, and the second hydrophilic region. These regions are formed on a surface of an electrical insulating substrate, and an electrophoresis lane is formed by the electrophoresis medium formed in the first hydrophilic region, the droplet supplied to the third hydrophilic region, the electrophoresis medium formed in the second hydrophilic region. In this case, the sample is subjected to electrophoresis separation by applying a voltage between the positive and negative electrodes, a predetermined position of the electrophoresis lane formed in the second region is irradiated with a light emitted from the light source, a fluorescence generated from fluorescent mark is detected by the photodetector, and the sample having been subjected to the electrophoresis separation is detected.

(5) An electrophoresis apparatus is provided, comprising an electrophoresis chip, and a constant temperature tank filled with insulating solution. The electrophoresis chip includes: a first hydrophilic region having a predetermined width, and a first length in a longitudinal direction for connecting first and second ends with each other, in which an electrophoresis medium is formed; a second hydrophilic region having a predetermined width, and a second length in the longitudinal direction for connecting first and second ends with each other, in which an electrophoresis medium is formed; a first region, in which a negative electrode is formed to be connected to the first end of the first hydrophilic region; a second region, in which a positive electrode is formed to be connected to the first end of the second hydrophilic region; a third hydrophilic region formed in a region of a gap, in which the second ends of the first and second hydrophilic regions face each other in the longitudinal direction, and adapted to receive a droplet of solution containing a fluorescent marked sample; and a first hydrophobic region surrounding the first region, the first hydrophilic region, the third hydrophilic region, the second region, and the second hydrophilic region. These regions are formed on a surface of an electrical insulating substrate, and an electrophoresis lane is formed by the electrophoresis medium formed in the first hydrophilic region, the droplet supplied to the third hydrophilic region, the electrophoresis medium formed in the second hydrophilic region. In this case, the electrophoresis portion of the electrophoresis chip is covered with the insulating solution.

(6) A method for producing an electrophoresis chip is provided, which comprises: a step of forming two electrodes in positions apart from each other by a predetermined distance on a surface of a glass substrate; a step of forming a hydrophobic film on the surface of the glass substrate excluding a region, in which the two electrodes are formed; a step of peeling off the hydrophobic film excluding a section of a predetermined length in a direction for connecting the two electrodes, and forming two hydrophilic films having thin and long shapes, and respectively connected to the two electrodes; and forming electrophoresis media in the two hydrophilic films.

(7) An electrophoresis chip is provided, which is constructed in a manner that pluralities of linear hydrophilic regions and hydrophobic regions are alternately formed in first and second substrates, the plurality of linear hydrophilic regions of the first and second substrates are placed to face each other, the first and second substrates are disposed away from each other by a predetermined gap, and an electrophoresis medium is held between the plurality of opposing linear hydrophilic regions of the first and second substrates.

(8) An electrophoresis chip is provided, which is constructed in a manner that a hydrophobic region and a linear hydrophilic region are formed on a surface of a substrate, buffer solution for electrophoresis is held on a surface of the hydrophilic region, and the buffer solution is covered with hydrophobic solution.

According to the present invention, a very small quantity of samples can be added, and an electrophoresis chip having high reproducibility of electrophoresis separation performance can be provided. In addition, electrophoresis chips can be mass-produced with high reproducibility.

What is claimed is:

1. An electrophoresis chip comprising:
   an electrical insulating substrate having a linear hydrophilic region in a longitudinal direction and a hydrophobic region adjacent to said hydrophilic region on a surface of said substrate;
   an electrophoresis medium, formed on said hydrophilic region of said substrate and having a gap in the medium in the longitudinal direction; and
   a pair of electrodes connected to both ends of said electrophoresis medium in said longitudinal direction.

2. The electrophoresis chip according to claim 1, wherein said substrate is glass.

3. The electrophoresis chip according to claim 1, wherein said electrophoresis medium is a gel.

4. The electrophoresis chip according to claim 1, wherein a sample is held in said gap.

5. The electrophoresis chip according to claim 1, wherein said gap is provided in a position close to one end from a center of said electrophoresis medium in said longitudinal direction.

6. The electrophoresis chip according to claim 5, wherein a length of a longer element medium of two element media of said electrophoresis medium divided into two parts by said gap is set in a range of 10 mm to 100 mm.

7. An electrophoresis chip, comprising:
   an electrical insulating substrate; and
   an electrophoresis medium, formed to be linear in a longitudinal direction on a surface of said substrate and having a gap in the medium in the longitudinal direction, wherein a region adjacent to said electrophoresis medium on said surface of said substrate is hydrophobic; and a length of said gap in said longitudinal direction of said electrophoresis medium is set in a range of 0.2 mm to 1 mm.

8. An electrophoresis chip comprising:

an electrical insulating substrate having a plurality of linear hydrophilic regions formed substantially parallel on a surface and a hydrophobic region adjacent to said hydrophilic regions;

a plurality of electrophoresis media, each formed on one of said plurality of hydrophilic regions of said substrate and having a gap in each electrophoretic media; and a pair of electrodes, one being connected to one end of each said plurality of electrophoresis media and the other being connected to the other end of each thereof.

9. An electrophoresis chip comprising:

an electrical insulating substrate having a plurality of liner hydrophilic regions formed substantially parallel on a surface of said substrate and a hydrophobic region adjacent to said hydrophilic regions;

a plurality of electrophoresis media, each formed on one of said hydrophilic regions of said substrate and having a gap in each of said electrophoretic media; and plural pairs of electrodes individually connected to both ends of each of said plurality of electrophoresis media.

10. An electrophoresis chip comprising:

an electrical insulating substrate having a thin and long hydrophilic region formed in a longitudinal direction on a surface of said substrate and a hydrophobic region formed surrounding said hydrophilic region; and an electrophoresis medium, formed on said hydrophilic region of said substrate and having a gap in the medium in the longitudinal direction, wherein an electrophoresis lane is formed by said electrophoresis medium and sample solution supplied to said gap.

11. The electrophoresis chip according to claim 1, wherein a width of said electrophoresis medium is set in a range of 0.1 mm to 5 mm.

* * * * *